(12) United States Patent
Dahl et al.

(10) Patent No.: US 8,017,654 B2
(45) Date of Patent: Sep. 13, 2011

(54) COMBINATION CANCER THERAPY WITH BIS(THIOHYDRAZIDE) AMIDE COMPOUNDS

(75) Inventors: Thomas A. Dahl, Cambridge, MA (US); Matthew McLeod, Boston, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 244 days.

(21) Appl. No.: 11/918,357

(22) PCT Filed: Apr. 13, 2006

(86) PCT No.: PCT/US2006/014531
§ 371 (c)(1),
(2), (4) Date: Aug. 25, 2008

(87) PCT Pub. No.: WO2006/113695
PCT Pub. Date: Oct. 26, 2006

(65) Prior Publication Data
US 2009/0137682 A1    May 28, 2009

Related U.S. Application Data

(60) Provisional application No. 60/672,139, filed on Apr. 15, 2005.

(51) Int. Cl.
*A01N 37/18* (2006.01)
*A61K 31/16* (2006.01)
*C07D 305/00* (2006.01)
*C07D 407/00* (2006.01)
*C07D 493/00* (2006.01)
*C07C 241/00* (2006.01)
*C07C 243/00* (2006.01)
*C07C 249/00* (2006.01)
*C07C 251/00* (2006.01)

(52) U.S. Cl. .................. 514/615; 549/510; 564/149
(58) Field of Classification Search .................. 514/615; 549/510; 564/149
See application file for complete search history.

(56) References Cited

U.S. PATENT DOCUMENTS

| | | |
|---|---|---|
| 4,012,360 A | 3/1977 | Schwarzenbach et al. |
| 4,822,777 A | 4/1989 | Abra |
| 4,826,866 A | 5/1989 | Taylor et al. |
| 5,300,278 A | 4/1994 | Pasqualini et al. |
| 5,498,421 A | 3/1996 | Grinstaff et al. |
| 5,560,933 A | 10/1996 | Soon-Shiong et al. |
| 5,665,382 A | 9/1997 | Grinstaff et al. |
| 5,739,686 A | 4/1998 | Naughton et al. |
| 5,753,200 A | 5/1998 | Zolotoochin et al. |
| 5,840,746 A | 11/1998 | Ducharme et al. |
| 5,843,400 A | 12/1998 | Fujibayashi et al. |
| 5,916,596 A | 6/1999 | Desai et al. |
| 6,013,836 A | 1/2000 | Hsu et al. |
| 6,096,331 A | 8/2000 | Desai et al. |
| 6,172,108 B1 | 1/2001 | Vega et al. |
| 6,172,188 B1 | 1/2001 | Thastrup et al. |
| 6,214,863 B1 | 4/2001 | Bissery et al. |
| 6,235,787 B1 | 5/2001 | Broadhurst et al. |
| 6,365,745 B1 | 4/2002 | Matsui et al. |
| 6,399,659 B2 | 6/2002 | Usui et al. |
| 6,435,787 B1 | 8/2002 | John |
| 6,455,515 B2 | 9/2002 | Gypser et al. |
| 6,506,405 B1 | 1/2003 | Desai et al. |
| 6,537,579 B1 | 3/2003 | Desai et al. |
| 6,656,971 B2 | 12/2003 | Wu et al. |
| 6,703,426 B1 | 3/2004 | Miles et al. |
| 6,749,868 B1 | 6/2004 | Desai et al. |

(Continued)

FOREIGN PATENT DOCUMENTS

AU    2006-228035 A1    10/2006
(Continued)

OTHER PUBLICATIONS

Chuiguk, V. A. and Nernazanyj A.G., "Mesoionic Methine Dyes from Biquaternary Salts of Dihetarylmethanes—1,3,4-Oxa(thia)diazoles and 1,2,4-Triazoles Derivatives," *Ukr. Khim. Zhurn.* 48:520 (1984).

(Continued)

*Primary Examiner* — Paddy Padmanabhan
*Assistant Examiner* — Sarah Pihonak
(74) *Attorney, Agent, or Firm* — McCarter & English LLP; Steven G. Davis

(57) ABSTRACT

A method of treating a subject with cancer includes the step of co-administering to the subject over three to five weeks, a taxane in an amount of between about 243 μmol/m2 to 315 μmol/m2 (e.g., equivalent to paclitaxel in about 210-270 mg/m2); and a bis(thiohydrazide amide) in an amount between about 1473 μmol/m2 and about 1722 μmol/m2 (e.g., Compound (1) in about 590-690 mg/m2). The bis(thiohydrazide amide) is represented by Structural Formula (I), Y is a covalent bond or an optionally substituted straight chained hydrocarbyl group, or, Y, taken together with both >C=Z groups to which it is bonded, is an optionally substituted aromatic group. $R_1$-$R_4$ are independently —H, an optionally substituted aliphatic group, an optionally substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring. $R_7$-$R_8$ are independently —H, an optionally substituted aliphatic group, or an optionally substituted aryl group. Z is O or S.

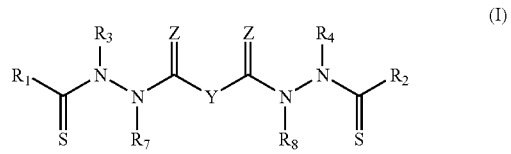

(I)

8 Claims, 3 Drawing Sheets

U.S. PATENT DOCUMENTS

| | | | |
|---|---|---|---|
| 6,753,006 B1 | 6/2004 | Desai et al. |
| 6,762,204 B2 | 7/2004 | Koya et al. |
| 6,800,660 B2 | 10/2004 | Koya et al. |
| 6,809,119 B2 | 10/2004 | Hu et al. |
| 6,825,235 B2 | 11/2004 | Chen et al. |
| 6,897,335 B2 | 5/2005 | Okabe et al. |
| 6,924,312 B2 | 8/2005 | Koya et al. |
| 7,001,923 B2 | 2/2006 | Koya et al. |
| 7,037,940 B2 | 5/2006 | Koya et al. |
| 7,074,952 B2 | 7/2006 | Chen et al. |
| 7,250,432 B2 | 7/2007 | Kwon et al. |
| 7,345,094 B2 | 3/2008 | Koya et al. |
| 7,368,473 B2 | 5/2008 | Koya et al. |
| 7,385,084 B2 | 6/2008 | Koya et al. |
| 7,435,843 B2 | 10/2008 | Chen et al. |
| 2002/0198160 A1 | 12/2002 | Everitt et al. |
| 2003/0195258 A1 | 10/2003 | Koya et al. |
| 2004/0022869 A1 | 2/2004 | Chen et al. |
| 2004/0225016 A1 | 11/2004 | Koya et al. |
| 2004/0235813 A1 | 11/2004 | Wanker et al. |
| 2005/0154039 A1 | 7/2005 | Glacera Contour |
| 2006/0142386 A1 | 6/2006 | Barsoum |
| 2006/0142393 A1 | 6/2006 | Sherman et al. |
| 2006/0167106 A1 | 7/2006 | Zhang et al. |
| 2006/0270873 A1 | 11/2006 | Chen et al. |
| 2007/0088057 A1 | 4/2007 | Lunsmann et al. |
| 2008/0089950 A1 | 4/2008 | Chen et al. |
| 2008/0118562 A1 | 5/2008 | Koya |
| 2008/0119440 A1 | 5/2008 | Koya |
| 2008/0146842 A1 | 6/2008 | Koya et al. |
| 2008/0176828 A1 | 7/2008 | Koya et al. |
| 2008/0214655 A1 | 9/2008 | Koya et al. |
| 2008/0226588 A1 | 9/2008 | McLeod |
| 2008/0242702 A1 | 10/2008 | Koya et al. |
| 2008/0269340 A1 | 10/2008 | Koya et al. |
| 2009/0005594 A1 | 1/2009 | Chen et al. |
| 2009/0023736 A1 | 1/2009 | Koya et al. |
| 2009/0042991 A1 | 2/2009 | Barsoum |
| 2009/0093538 A1 | 4/2009 | Bertin et al. |
| 2009/0137682 A1 | 5/2009 | Dahl |

FOREIGN PATENT DOCUMENTS

| | | |
|---|---|---|
| AU | 2006/228035 A1 | 11/2006 |
| CH | 482394 A | 12/1969 |
| DE | 2037257 | 2/1972 |
| DE | 2037257 A1 | 2/1972 |
| EP | 1454628 A | 9/2004 |
| EP | 1454628 A2 | 9/2004 |
| EP | 1493445 A | 1/2005 |
| EP | 1493445 A1 | 1/2005 |
| EP | 1406869 B1 | 9/2006 |
| EP | 1 731 148 A | 12/2006 |
| EP | 1731148 A1 | 12/2006 |
| EP | 1845083 A2 | 10/2007 |
| FR | 2097737 | 4/1972 |
| GB | 1 272 920 | 5/1972 |
| GB | 1272920 | 5/1972 |
| JP | 50-91056 | 7/1975 |
| JP | 63-267752 | 11/1988 |
| JP | 07-165693 | 6/1995 |
| JP | 182050 | 2/1996 |
| JP | 10-501215 | 2/1998 |
| WO | WO 94/10995 A1 | 5/1994 |
| WO | WO 99/34796 | 7/1999 |
| WO | WO 99/34796 A1 | 7/1999 |
| WO | WO 03/006428 A1 | 1/2003 |
| WO | WO 03/006429 A1 | 1/2003 |
| WO | WO 03/006430 A1 | 1/2003 |
| WO | WO 03/047524 A2 | 6/2003 |
| WO | WO 2004/064826 A1 | 8/2004 |
| WO | WO 2004/072051 A1 | 8/2004 |
| WO | WO 2005/028475 A2 | 3/2005 |
| WO | WO 2005/097758 A1 | 10/2005 |
| WO | WO 2006/009940 A1 | 1/2006 |
| WO | WO 2006/033913 A2 | 3/2006 |
| WO | WO 2006/055747 A2 | 5/2006 |
| WO | WO 2006/062732 A2 | 6/2006 |
| WO | WO 2006/089177 A2 | 8/2006 |
| WO | WO 2006/113493 A2 | 10/2006 |
| WO | WO 2006/113572 A1 | 10/2006 |
| WO | WO 2006/113695 A1 | 10/2006 |
| WO | WO 2006/124736 A2 | 11/2006 |
| WO | WO 2007/021881 A1 | 2/2007 |
| WO | WO 2007/021881 A2 | 2/2007 |
| WO | WO 2007/139955 A2 | 12/2007 |
| WO | WO 2008/024298 A1 | 2/2008 |
| WO | WO 2008/024299 A2 | 2/2008 |
| WO | WO 2008/024301 A2 | 2/2008 |
| WO | WO 2008/024302 A2 | 2/2008 |
| WO | WO 2008/024303 A2 | 2/2008 |
| WO | WO 2008/024305 A2 | 2/2008 |
| WO | WO 2008/027445 A2 | 3/2008 |
| WO | WO 2008/033300 A2 | 3/2008 |
| WO | WO 2008/033449 A2 | 3/2008 |
| WO | WO 2008/033494 A2 | 3/2008 |
| WO | WO 2008/082579 A1 | 7/2008 |
| WO | WO 2008/136976 A2 | 11/2008 |
| WO | WO 2009/020631 A2 | 2/2009 |
| WO | WO 2009/064374 A2 | 5/2009 |
| WO | WO 2009/073147 A2 | 6/2009 |
| WO | WO 2009/073148 A2 | 6/2009 |

OTHER PUBLICATIONS

"Remarks" paper as submitted by Applicant's Attorney.
Stalteri, M.A. et al., "Site-specific conjugation and labelling of prostate antibody 7E11C5.3 (CYT-351) with technetium-99m," *European Journal of Nuclear Medicine* 24(6):651-654, (1997).
Twomey, D., "Anticancer Agents-IX. Derivatives of Pyridine, Pyridazine and Phthalazine," *Proceedings of the Royal Irish Academy*, vol. 74, Sect. B:37-52,(1974).
Schwarz et al., CA77:48081, 1972.
Rupp, Walter, CA76:126992, 1972.
Barry, V. C. et al., "Anticancer Agents—III. Synthesis and Anticancer Activity of Some Bis-Thiosemicarbazones and Thoiosemicarbazides," *Proc. R.I.A. 65*:309-324 1967).
O'Callaghan, C. N., "Anticancer Agents X. Cyclisation of 1-Acyl-4-Alkylthiosemicarbazide Derivatives to 1,2,4-Triazoline-3-Thiones in the Presence of Hydrazine," *Proc. R.I.A. 74*:455-461 (1974).
Molina, P. et al., XP-01118868, "Methyl 2-Methyldithiocarbazate in Heterocyclic Synthesis: Preparation of 2,5-Disubstituted 1,3,4-Thiadiazoles, Bis(1,3,4-Thiadiazolium) Salts and Macrocycles Containing 1,3,4-Thiadiazole Subunits, X-Ray Crystal Structure of 2,2'-Bis[4,5-dihydro-5-(2-hydroxyethylimino)-4-methyl-1,3,4-thiadiazole]," *J. Chem. Soc. Perkin Trans. 1 s*, 5: 1159-1166 (1991).
Molina, P. et al., XP-001118802, "Preparation of a Novel Type of Ligands Incorporating Two or Three 1,3,4-Thiadiazole Units," *Heterocycles*, 36(6): 1263-1278 (1993).
Merlin, J.-L. et al., "In vitro Comparative Evaluation of Trastuzumab (Herceptin®) Combined with Paclitaxel (Taxol®) or Docetaxel (Taxotere®) in HER2-Expressing Human Breast Cancer Cell Lines," *Annals of Oncology*, vol. 13: 1743-1748 (2002).
Asahi Chemical Ind. K.K. Abstract of Japanese Patent No. 50-91056, Accession No. 47521Y/27 (1975).
Al-Talib, M. et al., "Diacyl Acid Dihydrazides," *Magnetic Resonance in Chemistry*, 28: 1072-1078 (1990).
Chuiguk, V.A., and Nemazanyi, A.G., "Mesoionic Methine Dyes of Biquaternary Salts of Diheteroaryl Methanes—Derivatives of 1, 3, 4—oxa (thia) Diazoles and 1, 2, 4—Triazoles," *Kiev. Gos. Univ., Kiev, USSR, Ukrainskii Khimicheskii Zhurnal, Russian Edition*, 50(5):519-524 (1984). Abstract, Accession No. 1984:630420, HCAPLUS Database.
Barrett, William G. and McKay, Donald, "Decomposition and Cycloaddition Reactions of Some Bis(azodicarbonyl) Compounds," *Journal of Chem. Soc.*, (4): 1046-1052 (1975).
Mitsui Toatsu Chem. Inc., Abstract of Japanese Patent No. 308024, published Dec. 25, 1986. From Derwent Publications Ltd.
Honshu Paper Mfg. Co. Ltd, Abstract of Japanese Patent No. 182050, published Feb. 13, 1996.
Rao et al., "Combination of Paclitaxel and Carboplatin as Second-Line Therapy for Patients with Metastatic Melanoma," *Cancer*, vol. 106, No. 2: 375-382 (2006).

Aug. 7, 2006, International Search Report, PCT/US2006/014531.
Aug. 7, 2006, Written Opinion of the International Searching Authority, PCT/US2006/014531.
Brittain et al., in *Polymorphism in Pharmaceutical Solids*, (NY: M. Dekker), vol. 95, pp. 348-361 (1999).
Goodman & Gilman's, The Pharmacological Basis of Therapeutics, Ninth Edition, (1996), Section X, Calabresi et al., pp. 1225-1232.
Gura et al., "Systems for Identifying New Drugs are Often Faulty," *Science*, 1997, 278: 1041-1042.
Johnson et al., "Relationships Between Drug Activity in NCI Preclinical in vitro and in vivo Models and Early Clinical Trials," *British J. of Cancer*, 2001, 84(10): 1424-1431.
Sausville et al., "Contributions to Human Tumor Xenografts to Anticancer Drug Development," *Cancer Research*, 2006, vol. 66, pp. 3351-3354.
Gehrmann, M., "Drug Evaluation: STA-4783—Enhancing Taxane Efficacy by Induction of Hsp70," *Current Opinion in Investigational Drugs*, 7(6): 574-580 (Jun. 2006), XP008087326.
"The Merck Manual," Chapter 14: Principles of Cancer Therapy, 1999 Merck Research Laboratories, pp. 987-995 (1999), XP002477370.
Wust, P. et al., "Hyperthermia in Combined Treatment of Cancer," *The Lancet Oncology*, 3(8): 487-497 (Aug. 2002), XP004813895.
Biagi, G. et al., "1,5-Diarylsubstituted 1,2,3-triazoles as Potassium Channel Activators. VI," *Il Farmaco*, 59(5): 397-404 (2004), esp. p. 398.
Patinit et al., "Bioisosterism: A Rational Approach in Drug Design," Chem. Rev., 96: 3147-3176 (1996), esp. p. 3152.
Balkwill, F. et al., "Inflammation and Cancer: Back to Virchow?" *The Lancet*, 357: 539-545 (Feb. 2001).
Jacquier-Sarlin, M.R. et al., "Protective Effects of hsp70 in Inflammation," *Experientia*, 50(11-12): 1031-1038 (Nov. 1994).
Cancer, Wikipedia, http://en.wikipedia.org/wiki/Cancer (1 of 40) Aug. 2, 2008 (all pages).
Abuchowski, A., et al., "Alteration of Immunological Properties of Bovine Serum Albumin by Covalent Attachment of Polyethylene Glycol," *The Journal of Biological Chemisty* 252(11):3578-3581 (1977).
Ashburner, M. and Bonner, J.J., "The Induction of Gene Activity in *Drosophila* by Heat Shock," *Cell*, 17: 241-254 (1979).
Auluck, P.K., et al., "Chaperone Suppression of α-Synuclein Toxicity in a *Drosophila* Model for Parkinson's Disease," *Science*, 295: 865-868 (2002).
Bahceci, et al., "Reactions of amidines with some carboxylic acid hydrazides," Indian Journal of Chemistry Section B, vol. 44B, 2005, pp. 568-572, XP009083365, p. 569, Scheme 1.
Barclay, J.W. and Roberson,R.M., "Role for Calcium in Heat Shock-Mediated Synaptic Thermoprotection in *Drosophila* Larvae," *J. Neurobiol.*, 56(4): 360-371 (2003).
Beck, F-X., et al., "Molecular Chaperones in the Kidney: Distribution, Putative Roles, and Regulation," *Am. J. Physiol. Renal. Physiol.*, 279: F203-F215 (2000).
Beillerot, et al., "Synthesis and protective effects of coumarin derivatives against oxidative stress induced by doxorubicin," Bioorganic & Medicinal Chemistry Letters, Oxford, GB, vol. 18, No. 3, Dec. 27, 2007, pp. 1102-1105, XP022475694, ISSN: 0960-894X.
Bellmann, K., et al., "Heat Shock Induces Resistance in Rat Pancreatic Islet Cells against Nitric Oxide, Oxygen Radicals and Streptozotocin Toxicity In Vitro," *J. Clin. Invest.*, 95(6): 2840-2845 (1995).
Berge, et al., "Pharmaceutical Salts," J. Pharm. Sci., 66 (1): 1-19, 1977.
Blondeau, N., et al., "Polyunsaturated Fatty Acids Induce Ischemic and Epileptic Tolerance," *Neuroscience*, 109(2): 231-241 (2002).
Calderwood S. R. et al,. "Extracellular Heat Schock Proteins in Cell Signaling and Immunity," *Annals of the New York Academy of Sciences*, 1113:28-29 (Oct. 2007).
Carmel, J.B., et al., "Mediators of Ischemic Preconditioning Identified by Microarray Analysis of Rat Spinal Cord," *Exp. Neurol.*, 185: 81-96 (2004).
Carter, R. J., et al., "Characterization of Progressive Motor Deficits in Mice Transgenic for the Human Huntington's Disease Mutation," *J. Neuroscience*, 19(8): 3248-3257 (1999).

Chen, H-C., et al., Induction of Heat Shock Protein 70 Protects Mesangial Cells Against Oxidative Injury, *Kidney Int.*, 56: 1270-1273 (1999).
Clathrate: Lewis, Hawley's Condensed Chemical Dictionary, 14th Edition, 1997, Van Nostrand Reinhold.
Craig, E. A., "The Heat Shock," *Crit. Rev. Biochem.*, 18(3): 239-280 (1985).
Daniels, G.A., et al., Nature Biotechnology, 22(9): 1125-1132 (Sep. 2004) (Epub Aug. 1, 2004).
Doi, Y., et al., "Effect of HSP70 Induced by Warm Ischemia to the Liver on Liver Function after Partial Hepatectomy," *Hepato-Gastroenterology*, 48: 533-540 (2001).
Dunn, S.E., et al., "Polystyrene-Poly (Ethylene Glycol) (PS-PEG2000) Particles as Model Systems for Site Specific Drug Delivery. 2. The Effect of PEG Surface Density on the in Vitro Cell Interaction and in Vivo Biodistribution," *Pharmaceutical Research* 11(7):1016-1022 (1994).
Dvorak, H.F., et al., "Identification and Characterization of the Blood Vessels of Solid Tumors That Are Leaky to Circulating Macromolecules," *American Journal of Pathology* 133(1):95-109 (1988).
Gabizon, A.A., "Selective Tumor Localization and Improved Therapeutic Index of Anthracyclines Encapsulated in Long-Circulating Liposomes," *Cancer Research* 52:891-896 (1992).
Gao, Y., et al., "Protein Kinase C-dependent Activation of P44/42 Mitogen-activated Protein Kinase and Heat Shock Protein 70 in Signal Transduction During Hepatocyte Ischemic Preconditioning," *World J. Gastroenterol.*, 10(7): 1019-1027 (2004).
Garloch, K., "Experimental Treatment Gives a Cancer Patient Hope," *The Charlotte Observer* [online], Apr. 25, 2005 [retrieved on May 23, 2008]. Retrieved from the Internet URL: http://www.ericandfran.com/charlotte_observer_april_25.htm.
Gavezzotti, "Are crystal structures predictable?," Accounts of Chemical Research, 27:309-314, 1994.
Gawande, N.G., et al., "Synthesis of some thiosemicarbazides and related compounds," CAPLUS, 1989, XP002391517.
Georgopoulos, C. and Welch, W. J., "Role of the Major Heat Shock Proteins as Molecular Chaperones," *Annu. Rev. Cell Biol.*, 9: 601-634 (1993).
Golub et al., "Molecular Classification of Cancer: Class Discovery and Class Prediction by Gene Expression Monitoring," *Science*, vol. 286, 1999, pp. 531-537.
Gref, R., et al., "Biodegradable Long-Circulating Polymeric Nanospheres," *Science* 263:1600-1603 (1994).
Gurney, M. E., et al., "Motor Neuron Degeneration in Mice That Express a Human Cu,Zn Superoxide Dismutase Mutation," *Science*, 264: 1772-1775 (1994).
Hiratsuka, M., et al., "Heat Shock Pretreatment Protects Pulmonary Isografts from Subsequent Ischemia-reperfusion Injury," *J. Heart Lung Transplant*, 17(12): 1238-1246 (1998).
Holcomb, L., et al., "Accelerated Alzheimer-Type phenotype in transgenic mice carrying both mutant *amyloid precursor protein* and *presenilin 1* transgenes," *Nature Medicine*, 4(1): 97-100 (1998).
Howland, D. S., et al., "Focal Loss of the Glutamate Transporter Eaat2 in a Transgenetic Rat Model of Sod1 Mutant-mediated Amyotrophic Lateral Sclerosis (ALS)," *Proc. Nat. Acad. Sci. USA*, 99(3): 1604-1609 (2002).
Ichihara, et al., "Roles of oxidative stress and Akt signaling in doxorubicin cardiotoxicity," Biochemical and Biophysical Research Communications, Academic Press Inc., Orlando, FL, US, vol. 359, No. 1, Jun. 2, 2007, pp. 27-33, XP022103137, ISSN: 0006-291X.
Inclusion complex: Lewis, Hawley's Condensed Chemical Dictionary, 14th Edition, 1997, Van Nostrand Reinhold.
Ishii, Y., et al., "Retinal Ganglion Cell Protection with Geranylgeranylacetone, a Heat Shock Protein Inducer, in a Rat Glaucoma Model," *Invest. Opthalmol. Vis. Sci.*, 44(5): 1982-1992 (2003).
Johnson, A.D., et al.,"Differential Distribution of 70-kD Heat Shock Protein Atherosclerosis," *Arterio Thromb Vasc Biol*, 15(1): 27-36 (1995).
Kandror, O. and Goldberg, A.L., "Trigger Factor is Induced Upon Cold Shock and Enhances Viability of *Escherichia coli* at Low Temperatures," *Proc Natl Acad Sci USA*, 94(10): 4978-4981 (1997).
Kelly, S. and Yenari, M.A., "Neuroprotection: Heat Shock Proteins," *Curr Res Med Opin*, 18(Suppl. 2): s55-s60 (2002).

Keswani, et al., "FK506 Is Neuroprotective in a Model of Antiretroviral Toxic Neuropathy," *Annals Neurology*, 53(1): 57-64 (2003).

Kiang, J.G. and Tsokos, G.C., "Heat Shock Protein 70 kDA: Molecular Biology, Biochemistry, and Physiology," *Pharmacol Ther*, 80(2): 183-201 (1998).

Klettner, A. and Herdegen, T., "The Immunophilin-Ligands FK506 and V-10,367 Mediate Neuroprotection by the Heat Shock Response," *Br J Pharmacol*, 138(5): 1004-1012 (2003).

Klettner, A., "The Induction of Heat Shock Proteins as a Potential Strategy to Treat Neurodegenerative Disorders," *Drug News Perspect*, 17(5): 299-306 (2004).

Klibanov, A., et al., "Amphipathic Polyethyleneglycols Effectively Prolong the Circulation Time of Liposōmes," *FEBS* 268(1):235-237 (1990).

Lang et al., Prevanlance of Exon 15 BRAF mutations in primary melanoma of the superficial spreading, nodular, acral and lentigo maligna subtypes, *J. Invest Dermatol.*, 125:575-579 (2005).

Langston, J.W., et al., "Selective Nigral Toxicity After Systemic Administration of 1-Methyl-4Phenyl-1,2,5,6-Tetrahydropyrine (MPTP) in the Squirrel Monkey," *Brain Res*, 292: 390-394 (1984).

Lee, J.E., et al.,"Differential Neuroprotection From Human Heat Shock Protein 70 Overexpression in in Vitro and in Vivo Models of Ischemia and Ischemia-Like Conditions," *Exp Neurol*, 170(1): 129-139 (2001).

Lepore, D.A., et al., "Role of Priming Stresses and Hsp70 in Protection From Ischemia-Reperfusion Injury in Cardiac and Skeletal Muscle," *Cell Stress & Chaperones*, 6(2): 93-96 (2001).

Lindquist, S., "The Heat-Shock Response," *Ann Rev Biochem*, 55: 1151-1191 (1986).

Longa, E.Z., et al., "Reversible Middle Cerebral Artery Occlusion Without Craniectomy in Rats," *Stroke*, 20(1): 84-91 (1989).

Malberg, J.E. and Seiden, L.S., Poster "MDMA Administration Induces Expression of HSP70 in the Rat Brain." Society for Neuroscience Annual Meeting, New Orleans, LA, Oct. 25-30, 1997.

Mangiarini, L., et al. , "Exon 1 of the *HD* Gene With an Expanded CAG Repeat is Sufficient to Cause a Progressive Neurological Phenotype in Transgenic Mice," *Cell*, 87: 493-506 (1996).

Marber, M.S., et al., "Overexpression of the Rat Inducible 70-kD Heat Stree Protein in a Transgenic Mouse Increases the Resistance of the Heart to Ischemic Injury," *J Clin Invest*, 95: 1446-1456 (1995).

Milas, et al., "Chemoradiotherapy: emerging treatment improvement strategies," published online Dec. 6, 2003 in Wiley InterScience (www.interscience.wiley.com).

Minowada, G. and Welch, W.J., "Clinical Implications of the Stress Response," *J Clin Invest*, 95: 3-12 (1995).

Morimoto, et al., In: The Biology of Heat Shock Proteins and Molecular Chaperone. (NY: Cold Spring Harbor Laboratory Press) pp. 417-455 (1994).

Mosser, D.D., et al., "The Chaperone Function of hsp70 is Required for Protecti Induced Apoptosis," *Mol Cell Biol*, 20(19): 7146-7159 (2000).

Papahadjopoulos, D., et al., "Sterically Stabilized Liposomes: Improvements in Pharmacokinetics and Antitumor Therapeutic Efficacy," *Proc. Natl. Acad. Sci. USA* 88:11460-11464 (1991).

Plumier, J.-C. L., et al., "Transgenic Mice Expressing the Human Heat Shock Protein 70 Have I proved Post-Ischemic Myocardial Recovery," *J Clin Invest*, 95: 1854-1860 (1995).

Radford, N.B., et al., "Cardioprotective Effects of 70-kDa Heat Shock Proteiin in Transgenic Mice," *Proc Natl Acad Sci USA*, 93(6): 2339-2342 (1996).

Renshaw, G.M.C., et al., "Oxygen Sensors and Energy Sensors Act Synergistically to Achieve a Graded Alteration in Gene Expression: Consequences for Assessing the Level of Neuroprotection in Response to Stressors," *Front Biosci*, 9: 110-116 (2004).

Sanchez, et al., "New naphthylcombretastatins. Modifications on the ethylene bridge," Bioorganic and Medicinal Chemistry, vol. 13, No. 6, Mar. 2005, pp. 2097-2107, XP002470852, ISSN: 0968-0896.

Sato, K., et al., "HSP70 is Essential to the Neuroprotective Effect of Heat-Shock," *Brain Res*, 740(1-2): 117-123 (1996).

Sauer, H. and Oertel, W.H., "Progressive Degeneration of Nigrostriatal Dopamine Neurons Following Instrastriatal Terminal Lesions with 6-Hydroxydopamine: A Combined Retrograde Tracing and Immunocytochemical Study in the Rat," *Neuroscience*, 59(2): 401-415 (1994).

Savage, E., et al., Living with Melanoma, [online], [retrieved on Aug. 9, 2006]. Retrieved from the Internet URL: http://ericandfran.com/melanona.htm.

Shin, K.D., et al., "Blocking tumor cell migration and invasion with biphenyl isoxazole derivative KRIBB3, a synthetic molecule that inhibits Hsp27 phosphorylation" *Journal of Biological Chemistry, American Society of Biolochemical Biologists*, Birmingham, US, vol. 280 No. 50, Oct. 18, 2005, pp. 41439-41448, XP002391924, ISN: 0021-9258.

Simon, M.M., et al., "Heat Shock Protein 70 Overexpression Affects the Response to Ultraviolet Light in Murine Fibroblasts," *J Clin Res*, 95(3): 926-933 (1995).

Sobue, G., Molecular Pathogenesis of Motor Neuron Diseases (In Japanese) English abstract, *Nihon Shinkei Seishin Yakurigaku Zasshi*, 21(1): 21-25 (2001).

Tanaka S., et al, "activation of T cells Recognizing an Epitipe of Heat-shock Protein 70 can protect against Rat Adjuvant Arthritis," *J. of Immunology* 163(10): 5560-5565 (1999).

Tavaria, M. et al., "A Hitchhiker's Guide to the Human Hsp70 Family," *Cell Stress Chaperones*, 1(1): 23-28 (1996).

Todryk, S.M., et al. "Facets of Heat Shock Protein 70 Show Immunotherapeutic Potential,", *Immunology*, 110(1): 1-9 (2003).

Tsuchiya, D., et al., "Overexpression of Rat Heat Shock Protein 70 Reduces Neuronal injury After Transient Focal Ischemia, Transient Global Ischemia, or Kainic Acid-Induced Seizures," *Neurosurgery*, 53(5): 1179-1188 (2003).

Valeriote, F., et al. "Synergistic Interaction of Anticancer Agents: A Cellular Perspective," *Cancer Chemotherapy Reports.*,59(5): 895-900 (1975).

Vippagunta, et al., "Crystalline solids," Advanced Drug Delivery Reviews, 48: 3-26, 2001.

Vleminckx, V., et al., "Upregulation of HSP27 in a Transgenic Model of ALS," *J Neuropathol Exp Neurol*, 61(11): 968-974 (2002).

Voss, R.M., et al., "Gender Differences in the Expression of Heat Shock Proteins: The Effect of Estrogen," *Am J Physiol Heart Circ Physiol*, 285: H687-H692 (2003).

Weichert et al., Taxol in malignant melanoma, J. *Natl. Cancer Inst. monogr.* 15:185-7 (1993 abstract only).

Yenari, M.A., "Heat Shock Proteins and Neuroprotection," *Adv Exp Med Biol*, 513: 281-299 (2002).

Yu, Q., et al., "Retinal Uptake of Hsc/Hsp70 Intravitreally Injected and its Effect on Susceptibility to Light Damage," *Molecular Vision*, 7: 48-56 (2001).

Zhang, Y., et al., "Estrogen and Androgen Protection of Human Neurons Against Intracellular Amyloid $\beta_{1-42}$ Toxicity Through Heat Shock Protein 70," *J Neuroscience*, 24(23): 5315-5321 (2004).

International Search Report for International Application No. PCT/US2006/014531, mailed: Jul. 8, 2006.

"Activating Agents and Protecting Groups," *Handbook of Reagents for Organic Synthesis*, pp. 133-135.

Badawy, M. A., "Synthesis and Reactions of 1,2,4-Triazino-1,2,4-Triazines," *Sulfur Letters* 11(1+2):21-28 (1990).

Baker, W., et al., "663: 1 : 4-*Diaryl*-1: 4-*dihydro*-1 : 2 : 4 : 5-*tetrazines and Derived Substances*," Journal of the Chemical Society, 3389-3394 (1950).

Barta-Szalai, G., et al., "Electron Deficient Heteroaromatic Ammonioamidates. XVII. N-(3-Quinazolinio)amidates. VI. The Photochemistry of N-(3-Quinazolinio)amidates in the Presence of ÿ-Toluenethiol," *Acta Chemica Scandinavica B* 33:79-85 (1979).

Branch, C. L., et al., "Synthesis of 6-Hydroxy-2-Methyl-3-Thioxo-2H-1,2,4-Triazin-5-one," *Synthetic Communications* 26(11):2075-2084 (1996).

Cava, M.P., et al., "Thionation Reactions of Lawesson's Reagents," *Tetrahedron*, 14(22): 5061-5087 (1985).

El-Barbary, A.A., et al., "Studies in Organophosphorus Compounds," *Tetrahedron*, 36: 3309-3315 (1980).

Greene, T. W. et al., "Protection for the Amino Group," *Protective Groups in Organic Synthesis*, Third Edition, 7, pp. 494-653.

Greene, T. W. et al., "Protection for the Carboxyl Group," *Protective Groups in Organic Synthesis*, Third Edition, 5, pp. 369-453.

Heindel, N.D., et al., "Thiohydrazides and Acetylene Esters, A New Route to 1,3,4-Thiadiazoles," *Journal of Heterocyclic Chemistry*, 17(1): 191-193 (1980).

Henderson, N. D. et al., "Synthesis of new bifunctional compounds which selectively alkylate guanines in DNA," *Anti-Cancer Drug Design*, 13:749-768 (1998).

Jensen, K. A., et al., "Thiohydrazides and Thiohydrazones: A New Class of Antibacterial Substances," *Acta Chemica Scandinavica*, 6(Pt. II): 957-958 (1952).

Metzner, P. et al., "Sulfur Reagents in Organic Synthesis," *Best Synthetic Methods*, pp. 30-53, 182-185.

Mohamed, M. M., et al., "Synthesis & Some Reactions of 2-(α/β—Naphthyl)-3,1-benzoxazin-4(*H*)-ones 3-Amino-2-(ÿ-naphthyl)quinazolin-4(3*H*)-one," *Indian Journal of Chemistry* 25B(2):207-211 (1986).

Molina, P., et al., "Methyl 2-Methyldithiocarbazate in Heterocyclic Synthesis: Preparation of 2,5-Disubstituted 1,3,4-Thiadiazoles, Bis(1,3,4-Thiadiazolium) Salts and Macrocycles containing 1,3,4-Thiadiazole Subunits, X-Ray Crystal Structure of 2,2'-Bis[4,5-dihydro-5-(2-hydroxyethylimino)-4-methyl-1,3,4-thiadiazole]," *J. Chem. Soc. Perkin Trans. 1 s* 5:1159-1166 (1991).

Molina, P., et al., "Preparation of a Novel Type of Ligands Incorporating Two or Three 1,3,4-Thiadiazole Units," *Heterocycles* 36(6):1263-1278 (1993).

Przheval, N. M., et al., "A New General Synthesis of Bistetrafluoroborates of 2,3,4,5-Tetrasubstituted 1,3,4-Thiadiazoliums," *Synthesis* 5:463-464 (1993).

Sato, T., et al., "Studies in Organic Sulfur Compounds. I. Thioformyl Phenylhydrazide," *Bulletin of the Chemical Society of Japan*, 27(9): 624-627 (1954).

Tsuji, T., et al., "Synthesis and Reactions of N-Aminothiouracils and Thiadiazolo [3,2-ÿ] pyrimidinones," *Chem. Pharm. Bull.* 26(9):2765-2767 (1978).

Ueda, H. and Ohta, M., "Studies on Sulfur-Containing Heterocyclic Compounds," *Nippon Kagaku Zasshi*, 80:571-574 (1959).

Walter, W., et al. , "Chapter 9: The Chemistry of the Thiohydrazide Group," *The Chemistry of Amides* (Ed. J. Zabicky), (London: Interscience Publishers), pp. 477-514 (1970).

"REMARKS" paper as submitted by applicant's attorney, (2005).

Atherton, F.R., et al., "Synthesis of 3(*S*)-Acylamino-1-[(Phenyl)(1H-Tetrazol-5-YL)Amino]-2-Azetidinones," *Tetrahedron*, 39(15): 2599-2608 (1983).

Chuyguk, V. A. and Nemazanyj A.G., "Mesoionic Methine Dyes from Biquatemary Salts of Dihetarylmethanes—1,3,4-Oxa(thia)diazoles and 1,2,4-Triazoles Derivatives," *Ukr. Khim. Zhurn.* 48:520 (1984).

Daniels, G., et al., "A simple method to cure established tumors by inflammatory killing of normal cells," Nature Biotechnoloyg, Sep. 2004, 22(9), 1125-1132 (Epub Aug. 1, 2004).

Garlock, K., "Experimental Treatment Gives a Cancer Patient Hope," *The Charlotte Observer* [online], Apr. 25, 2005 [retrieved on May 23, 2008]. Retrieved from the Internet URL: http://www.ericandfran.com/charlotte_observer_april_25.htm.

Goodman & Gilmam's, The Pharmacological Basis of Therapeutics, Ninth Edition, (1996), Section X, Calabresi et al., pp. 1225-1232.

Barry, V.C. et al., "Anticancer Agents-III. Synthesis and Anticancer Activity of Some Bis-Thiosemicarbazones and Thiosemicarbazides," *Proc. R.I.A.*, 65: 309-324 (1967).

Johnson, A.D., et al., "Differential Distribution of 70-kD Heat Shock Protein Atherosclerosis," *Arterio Thromb Vasc Biol*, 15(1): 27-36 (1995).

Kruse, L.I., et al., "Some Benzyl-Substituted Imidazoles, Triazoles, Terazoles, Pyridinethiones, and Structural Relatives as Multisubstrate Inhibitors of Dopamine β-Hydroxylase. 4.[1] Structure-Activity Relationships at the Copper Binding Site," *J. Med. Chem.*, 33: 781-789 (1990).

Lee, J.E., et al., "Differential Neuroprotection From Human Heat Shock Protein 70 Overexpression in in Vitro and in Vivo Models of Ischemia and Ischemia-Like Conditions," *Exp Neurol*, 170(1): 129-139 (2001).

Marber, M.S., et al., "Overexpression of the Rat Iducible 70-kD Heat Stree Protein in a Transgenic Mouse Increases the Resistance of the Heart to Ischemic Injury," *J Clin Invest*, 95: 1446-1456 (1995).

McCarthy, A.R., et al., "Cyclic Meso-ionic Compounds. Part IX.[1] Synthesis, Spectroscopic Properties, and Chemistry of 1,3,4-Thiadiazolium-2-olates and 1,3,4-Oxadiazolium-2-thiolates[2]," *J.C.S. Perkin I*, 627-632 (1974).

Bräuniger, H., "Hydrazide und Hydrazidderivate von Dicarbonsäuren," Pharmaceutical-Chemical Institute of University of Rostock, Supplied by the "British Library," *Pharmazie*, 25(5-6): 279-283 (1970).

Calderwood, S., et al., "Extracellular heat shock proteins in cell signaling and immunity,"Annals of the New York Academy of Sciences, Oct. 2007, 1113, 28-39.

O'Callaghan, C.N., "Anticancer Agents-X. Cyclisation of 1-Acyl-4-Alkylthiosemicarbazide Derivatives to 1,2,4-Triazoline-3-Thiones in the Presence of Hydrazine," *Proc. R.I.A.*, 74: 455-461 (1974).

Patani, et al., "Bioisosterism: A Rational Approach in Drug Design," Chem. Rev., 96: 3147-3176 (1996).

Notification of Transmittal of the International Preliminary Examination Report for International Application No. PCT/US 02/21716, mailed Sep. 19, 2003.

Notification of Transmittal of the International Search Report or the Declaration for International Application No. PCT/US 02/21716, mailed Nov. 15, 2002.

Notification of Transmittal of the Written Opinion of the International Searching Authority for International Application No. PCT/US 02/21716, mailed Feb. 20, 2003.

Rao et al., Cancer, vol. 106, No. 2: 375-382 (2006).

Schroeter, G., et al., "Über methionsäure und deren verwendung zu synthesen," Instit der Kgl. Tierärztlichen Hochschule Berlin, Oct. 26, 1918; pp. 161-257.

Shin, K.D., et al., "Blocking tumor cell migration and invasion with biphenyl isoxazole derivative KRIBB3, a synthetic molecule that inhibits Hsp27 phosphorylation" Journal of Biological Chemistry, American Society of Biolochemical Biologists, Birmingham, US, vol. 280 No. 50, Oct. 18, 2005, pp. 41439-41448, XP002391924, ISSN: 0021-9258.

Stalteri, M.A., et al., "Site-specific conjugation and labelling of prostate antibody 7E1105.3 (CYT-351) with technetium-99m," *European Journal of Nuclear Medicine* 24(6):651-654, (1997).

Sun, et al., Shengwu Huaxue Yu Shengwu Wuli Xuebao, 4(5), 539-550 (1964). (English Abstract).

Tanaka, S., et al., "Activiation of T cells recognizing an epitope of heat-shock protein 70 can protect against rat adjuvant arthritis," Journal of Immunology, Nov. 1999, 163(10), 5560-5565.

Biagi, G. et al.,"1,5-Diarylsubstituted 1,2,3-triazoles as Potassium Channel Activators. VI," *Il Farmaco*, 59(5): 397-404 (2004), esp. p. 398.

Zinner, G., et al., "Über 2-Adamantylhydrazin und einige seiner Vorstufen und Derivate," *Arch. Pharm.* (Weinheim), 317: 1024-1028 (1984).

Gawande, N.G. et al., "Synthesis of Some Thiosemicarbazides and Related Compounds," CAPLUS, 1989, pp. 1-2.

Wiernik, P.H., et al., "Taxol in Malignant Melanoma," *J. Natl. Cancer Inst. Monogr.*, 15: 185-187 (1993) (abstract only).

http://www.ericandfran.com/melanoma.htm; STA-4783 with Taxol; Relevant article publication date is believed to be Dec. 2004.

http://www.ericandfran.com/charlotte_observer_april_25.htm; The Charlotte Observer; Apr. 25, 2005.

COMBINATION CANCER THERAPY WITH BIS(THIOHYDRAZIDE) AMIDE COMPOUNDS

RELATED APPLICATION

This application is the U.S. National Stage of International Application No. PCT/US2006/014531, filed Apr. 13, 2006, published in English, which claims priority under 35 U.S.C. §119 or 365 to U.S. Provisional Application No. 60/672,139, filed on Apr. 15, 2005. The entire teachings of the above applications are incorporated herein by reference.

BACKGROUND OF THE INVENTION

The taxanes are an important class of anticancer agents. In particular, Taxol™ (paclitaxel) is an effective anticancer agent, especially in the treatment of ovarian cancer, metastatic breast cancer, non-small cell lung cancer (NSCLC) and AIDS-related Kaposi's sarcoma. However, there is still a significant need in the art for improvement in the efficacy of paclitaxel therapy, both in terms of the proportion of patients who respond to therapy and the survival benefit imparted. Moreover, administration of Taxol has side effects, including reducing immune function by reducing natural killer (NK) cell activity.

In an attempt to improve efficacy, paclitaxel is sometimes used in combination with other anticancer agents. For example, carboplatin in the treatment of NSCLC. Such combinations can have an additive benefit or increased response rate, but can tend to also combine the side effect profiles of each agent. Other agents have been researched, for example, bis(thiohydrazide amides) have been tested in animal models as described in U.S. Pat. Nos. 6,800,660, 6,762,204, U.S. patent application Ser. Nos. 10/345,885 filed Jan. 15, 2003, and 10/758,589, Jan. 15, 2004, the entire teachings of which are incorporated herein by reference.

However, there is still an urgent need for particular combination therapies that can enhance the antitumor effects of paclitaxel without further increasing side effects suffered by patients.

SUMMARY OF THE INVENTION

It is now found that certain bis(thiohydrazide) amide and taxane combinations are surprisingly effective at treating subjects with cancer without further increasing side effects. The particular combination therapies disclosed herein demonstrate surprising biological activity by raising Hsp70 levels (see Example 3), by demonstrating significant anticancer effects (see Examples 4-5), and by halting or reversing side effects (see Examples 4-5) such as the reduction in natural killer (NK) cell activity typically associated with Taxol™ administration.

A method of treating a subject with cancer includes the step of co-administering to the subject over three to five weeks, a taxane in an amount of between about 243 µmol/m2 to 315 µmol/m2 (e.g., equivalent to paclitaxel in about 210-270 mg/m2); and a bis(thiohydrazide amide) in an amount between about 1473 µmol/m2 and about 1722 µmol/m2 (e.g., Compound (1) in about 590-690 mg/m²). The bis(thiohydrazide amide) is represented by Structural Formula I:

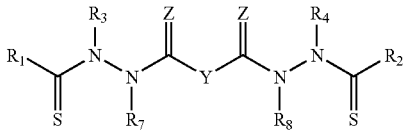

Y is a covalent bond or an optionally substituted straight chained hydrocarbyl group, or, Y, taken together with both >C=Z groups to which it is bonded, is an optionally substituted aromatic group.

$R_1$-$R_4$ are independently —H, an optionally substituted aliphatic group, an optionally substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring.

$R_7$-$R_9$ are independently —H, an optionally substituted aliphatic group, or an optionally substituted aryl group.

Z is O or S.

In various embodiments, a method of treating a subject with cancer includes administering to the subject effective amounts of each of a platinum anticancer compound; a taxane or a pharmaceutically acceptable salt or solvate thereof, and a bis(thiohydrazide amide) represented by Structural Formula I or a pharmaceutically acceptable salt or solvate thereof.

In various embodiments, a method of treating a subject with cancer includes administering to the subject once every three weeks, independently or together a taxane in an amount of about 205 µmol/m2 (e.g., paclitaxel in about 175 mg/m2); and a bis(thiohydrazide amide) represented by Structural Formula I or a pharmaceutically acceptable salt or solvate thereof in an amount between about 220 µmol/m2 and about 1310 µmol/m2 (e.g., Compound (1) in about 88-525 mg/m2).

In various embodiments, a pharmaceutical composition includes a pharmaceutically acceptable carrier or diluent. In some embodiments, the molar ratio of bis(thiohydrazide amide) to taxane can be between about 5.5:1 and about 5.9:1, in certain embodiments, between about 2.7:1 and about 2.9:1, and in particular embodiments, between about 4.1:1 and about 4.5:1.

In various embodiments, the invention includes the use of a bis(thiohydrazide amide) for the manufacture of medicament for treating cancer in combination with a taxane in each of the molar ratios described above. In some embodiments, the invention includes the use of a bis(thiohydrazide amide) and taxane for the manufacture of medicament for treating cancer in each of the molar ratios described above.

The taxanes employed in the invention, e.g., paclitaxel, are described in the Detailed Description section below.

In various embodiments, a pharmaceutically acceptable salt or solvate of either the bis(thiohydrazide)amide or taxane anticancer agents can be employed, optionally with a pharmaceutically acceptable carrier or diluent. In certain embodiments, a pharmaceutical composition includes the bis(thiohydrazide) amide, the taxane, and a pharmaceutically acceptable carrier or diluent.

The methods are particularly effective for treating the claimed cancers as demonstrated in the Examples, and halting or reversing side effects such as the reduction in natural killer (NK) cell activity typically associated with Taxol™ administration.

DETAILED DESCRIPTION OF THE INVENTION

Figure 1A:
FIGS. 1A, 1B, and 1C are bar graphs showing the percent increase in Hsp70 plasma levels associated with administration of the Compound (1)/paclitaxel combination therapy at 1 hour (FIG. 1A), 5 hours (FIG. 1B), and 8 hours (FIG. 1C) after administration.

A description of preferred embodiments of the invention follows.

In various embodiments, a method of treating a subject with cancer includes the step of co-administering to the subject over three to five weeks, a taxane in an amount of between about 243 μmol/m2 to 315 μmol/m2 (e.g., equivalent to paclitaxel in about 210-270 mg/m2); and a bis(thiohydrazide amide) (e.g., as represented by Structural Formula I) in an amount between about 1473 mmol/m2 and about 1722 μmol/m2 (e.g., Compound (1) in about 590-690 mg/m2).

A subject, e.g., typically a human subject, can be treated for any cancer described herein. Typically, the cancer can be a soft tissue sarcoma (e.g., typically soft tissue sarcomas other than GIST) or metastatic melanoma. In some embodiments, the cancer is metastatic melanoma.

In some embodiments, the taxane and the bis(thio-hydrazide) amide can each be administered in three equal weekly doses for three weeks of a four week period. In preferred embodiments, the four week administration period can be repeated until the cancer is in remission.

The taxane can be any taxane defined herein. In particular embodiments, the taxane is paclitaxel intravenously administered in a weekly dose of about 94 μmol/m2 (80 mg/m2).

In various embodiments, the bis(thiohydrazide amide) can be intravenously administered in a weekly dose of between about 500 μmol/m2 and about 562 μmol/m2, or more typically in a weekly dose of about 532 μmol/m2. (e.g., Compound (1) in about 590-690 mg/m2).

In some embodiments, the subject is treated for metastatic melanoma. In certain embodiments, the subject is treated for soft tissue sarcomas other than GIST.

In preferred embodiments, a method of treating a human subject with cancer includes intravenously administering to the subject in a four week period, three equal weekly doses of paclitaxel in an amount of about 94 μmol/m2; and a bis(thiohydrazide amide) represented by the following Structural Formula:

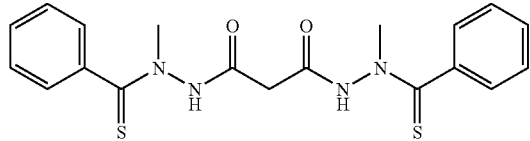

or a pharmaceutically acceptable salt or solvate thereof in an amount of about 532 μmol/m2. Typically, the cancer is a soft tissue sarcomas (e.g., typically soft tissue sarcomas other than GIST) or metastatic melanoma.

In various embodiments, the subject can be intravenously administered between about 220 μmol/m2 and about 1310 μmol/m2 (e.g., Compound (1) in about 88-525 mg/m2) of the bis(thiohydrazide amide) once every 3 weeks, generally between about 220 μmol/m2 and about 1093 μmol/m2 (e.g., Compound (1) in about 88-438 mg/m2) once every 3 weeks, typically between about 624 jμmol/m2 and about 1124 μmol/m2 m2 (e.g., Compound (1) in about 250-450 mg/m2), more typically between about 811 μmol/m2 and about 936 μmol/m2 m2 (e.g., Compound (1) in about 325-375 mg/m2), or in particular embodiments, about 874 jμmol/m2 ((e.g., Compound (1) in about 350 mg/m2). In particular embodiments, the subject can be intravenously administered between about 582 μmol/m2 and about 664 μmol/m2 (e.g., Compound (1) in about 233-266 mg/m2) of the bis(thiohydrazide amide) once every 3 weeks. In certain embodiments, the bis(thiohydrazide amide) is in an amount of about 664 μmol/m2 (e.g., Compound (1) in about 266 mg/m2).

In various embodiments, the subject can be intravenously administered between about 200 μmol/m2 to about 263 μmol/m2 of the taxane as paclitaxel once every 3 weeks (e.g., paclitaxel in about 175-225 mg/m2). In some embodiments, the subject can be intravenously administered between about 200 mmol/m2 to about 234 μmol/m2 of the taxane as paclitaxel once every 3 weeks (e.g., paclitaxel in about 175-200 mg/m2). In certain embodiments, the paclitaxel is administered in an amount of about 234 μmol/m2 (200 mg/m2). In certain embodiments, the paclitaxel is administered in an amount of about 205 μmol/m2 (175 mg/m2)

In various embodiments, the taxane, e.g., paclitaxel, and the bis(thiohydrazide amide), e.g., Compound (1), can be administered together in a single pharmaceutical composition.

In various embodiments, a method of treating a subject with cancer includes administering to the subject once every three weeks, independently or together a taxane in an amount of about 205 μmol/m2 (e.g., paclitaxel in about 175 mg/m2); and a bis(thiohydrazide amide) represented by Structural Formula I or a pharmaceutically acceptable salt or solvate thereof in an amount between about 220 μmol/m2 and about 1310 μmol/m2 (e.g., Compound (1) in about 88-525 mg/m2). Typically, the taxane is paclitaxel intravenously administered in an amount of about 205 μmol/m2. The bis(thiohydrazide amide) can typically be intravenously administered between about 220 μmol/m2 and about 1093 μmol/m2 (e.g., Compound (1) in about 88-438 mg/m2), more typically between about 749 μmol/m2 and about 999 μmol/m2 (e.g., compound (1) in about 300-400 mg/m2), in some embodiments between about 811 μmol/m2 and about 936 jμmol/m2 (e.g., Compound (1) in about 325-375 mg/m2). In certain embodiments, the bis(thiohydrazide amide) can be Compound (1) intravenously administered between about 874 μmol/m2 (about 350 mg/m2).

In a particular embodiment, a method of treating a subject with cancer includes intravenously administering to the subject in a single dose per three week period: paclitaxel in an amount of about 205 μmol/m2 (175 mg/m2); and Compound (1) or a pharmaceutically acceptable salt or solvate thereof in an amount of about 874 μmol/m2 (350 mg/m2), wherein the cancer is a soft tissue sarcomas other than GIST or metastatic melanoma.

In various embodiments, a pharmaceutical composition includes a pharmaceutically acceptable carrier or diluent; and a molar ratio of a bis(thiohydrazide amide) to a taxane between about 5.5:1 and about 5.9:1, wherein the bis(thiohydrazide amide) represented by Structural Formula I or a pharmaceutically acceptable salt or solvate thereof. In some embodiments, the molar ratio of the bis(thiohydrazide amide) to the taxane is between about 5.6:1 and about 5.8:1, or more typically, about 5.7:1. In certain embodiments, the taxane is paclitaxel or a pharmaceutically acceptable salt or solvate thereof. In particular embodiments, the bis(thiohydrazide amide) is Compound (1).

In various embodiments, a pharmaceutical composition includes a pharmaceutically acceptable carrier or diluent; and a molar ratio of a bis(thiohydrazide amide) to a taxane between about 2.6:1 and about 3.0:1, wherein the bis(thiohydrazide amide) represented by Structural Formula I or a pharmaceutically acceptable salt or solvate thereof. In some embodiments, the molar ratio of the bis(thiohydrazide amide) to the taxane is between about 2.7:1 and about 2.9:1, or more typically, about 2.8:1. In certain embodiments, the taxane is paclitaxel or a pharmaceutically acceptable salt or solvate thereof. In particular embodiments, the bis(thiohydrazide amide) is Compound (1).

In various embodiments, a pharmaceutical composition includes a pharmaceutically acceptable carrier or diluent; and a molar ratio of a bis(thiohydrazide amide) to a taxane between about 4.1:1 and about 4.5:1, wherein the bis(thiohydrazide amide) represented by Structural Formula I or a pharmaceutically acceptable salt or solvate thereof. In some embodiments, the molar ratio of the bis(thiohydrazide amide) to the taxane is between about 4.2:1 and about 4.4:1, or more typically, about 4.3:1. In certain embodiments, the taxane is paclitaxel or a pharmaceutically acceptable salt or solvate thereof. In particular embodiments, the bis(thiohydrazide amide) is Compound (1).

In various embodiments, the invention includes the use of a bis(thiohydrazide amide) for the manufacture of medicament for treating cancer in combination with a taxane in a molar ratio of bis(thiohydrazide amide) to taxane between about 5.5:1 and about 5.9:1, typically between about 5.6:1 and about 5.8:1, more typically about 5.7:1, wherein the bis(thiohydrazide amide) is represented by Structural Formula I. In some embodiments, the molar ratio of bis(thiohydrazide amide) to taxane can be between about 2.6:1 and about 3.0:1, typically between about 2.7:1 and about 2.9:1, more typically about 2.8:1. In some embodiments, the molar ratio of bis(thiohydrazide amide) to taxane can be between about 4.1:1 and about 4.5:1, typically between about 4.2:1 and about 4.4:1, more typically about 4.3:1.

In various embodiments, the invention includes the use of a bis(thiohydrazide amide) and taxane for the manufacture of medicament for treating cancer in a molar ratio of bis(thiohydrazide amide) to taxane between about 5.5:1 and about 5.9:1, typically between about 5.6:1 and about 5.8:1, more typically about 5.7:1, wherein the bis(thiohydrazide amide) is represented by Structural Formula I. In some embodiments, the molar ratio of bis(thiohydrazide amide) to taxane can be between about 2.6:1 and about 3.0:1, typically between about 2.7:1 and about 2.9:1, more typically about 2.8:1. In some embodiments, the molar ratio of bis(thiohydrazide amide) to taxane can be between about 4.1:1 and about 4.5:1, typically between about 4.2:1 and about 4.4:1, more typically about 4.3:1.

The bis(thiohydrazide amides) employed in the disclosed invention are represented by Structural Formula I, or a pharmaceutically acceptable salt or solvate thereof.

In one embodiment, Y in Structural Formula I is a covalent bond, —C($R_5R_6$)—, —($CH_2CH_2$)—, trans-(CH=CH)—, cis-(CH=CH)— or —(C≡C)— group, preferably —C($R_5R_6$)—. $R_1$-$R_4$ are as described above for Structural Formula I. $R_5$ and $R_6$ are each independently —H, an aliphatic or substituted aliphatic group, or $R_5$ is —H and $R_6$ is an optionally substituted aryl group, or, $R_5$ and $R_6$, taken together, are an optionally substituted C2-C6 alkylene group. The pharmaceutically acceptable cation is as described in detail below.

In specific embodiments, Y taken together with both >C=Z groups to which it is bonded, is an optionally substituted aromatic group. In this instance, certain bis(thiohydrazide amides) are represented by Structural Formula II:

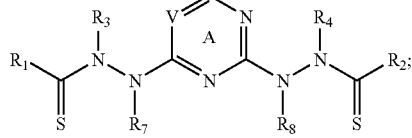

wherein Ring A is substituted or unsubstituted and V is —CH— or —N—. The other variables in Structural Formula II are as described herein for Structural Formula I or III.

In particular embodiments, the bis(thiohydrazide amides) are represented by Structural Formula III:

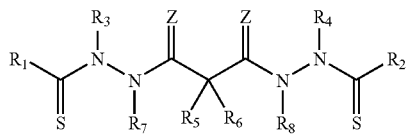

$R_1$-$R_8$ and the pharmaceutically acceptable cation are as described above for Structural Formula I.

In Structural Formulas I-III, $R_1$ and $R_2$ are the same or different and/or $R_3$ and $R_4$ are the same or different; preferably, $R_1$ and $R_2$ are the same and $R_3$ and $R_4$ are the same. In Structural Formulas I and III, Z is preferably O. Typically in Structural Formulas I and III, Z is O; $R_1$ and $R_2$ are the same; and $R_3$ and $R_4$ are the same. More preferably, Z is O; $R_1$ and $R_2$ are the same; $R_3$ and $R_4$ are the same, and $R_7$ and $R_8$ are the same.

In other embodiments, the bis(thiohydrazide amides) are represented by Structural Formula III: $R_1$ and $R_2$ are each an optionally substituted aryl group, preferably an optionally substituted phenyl group; $R_3$ and $R_4$ are each an optionally substituted aliphatic group, preferably an alkyl group, more preferably, methyl or ethyl; and $R_5$ and $R_6$ are as described above, but $R_5$ is preferably —H and $R_6$ is preferably —H, an aliphatic or substituted aliphatic group.

Alternatively, $R_1$ and $R_2$ are each an optionally substituted aryl group; $R_3$ and $R_4$ are each an optionally substituted aliphatic group; $R_5$ is —H; and $R_6$ is —H, an aliphatic or substituted aliphatic group. Preferably, $R_1$ and $R_2$ are each an optionally substituted aryl group; $R_3$ and $R_4$ are each an alkyl group; and $R_5$ is —H and $R_6$ is —H or methyl. Even more preferably, $R_1$ and $R_2$ are each an optionally substituted phenyl group; $R_3$ and $R_4$ are each methyl or ethyl; and $R_5$ is —H and $R_6$ is —H or methyl. Suitable substituents for an aryl group represented by $R_1$ and $R_2$ and an aliphatic group represented by $R_3$, $R_4$ and $R_6$ are as described below for aryl and aliphatic groups.

In another embodiment, the bis(thiohydrazide amides) are represented by Structural Formula III: $R_1$ and $R_2$ are each an optionally substituted aliphatic group, preferably a C3-C8 cycloalkyl group optionally substituted with at least one alkyl group, more preferably cyclopropyl or 1-methylcyclopropyl; $R_3$ and $R_4$ are as described above for Structural Formula I, preferably both an optionally substituted allyl group; and $R_5$ and $R_6$ are as described above, but $R_5$ is preferably —H and $R_6$ is preferably —H, an aliphatic or substituted aliphatic group, more preferably —H or methyl.

Alternatively, the bis(thiohydrazide amides) are represented by Structural Formula III: $R_1$ and $R_2$ are each an optionally substituted aliphatic group; $R_3$ and $R_4$ are as described above for Structural Formula I, preferably both an optionally substituted alkyl group; and $R_5$ is —H and $R_6$ is —H or an optionally substituted aliphatic group. Preferably, $R_1$ and $R_2$ are both a C3-C8 cycloalkyl group optionally substituted with at least one alkyl group; $R_3$ and $R_4$ are both as described above for Structural Formula I, preferably an alkyl group; and $R_5$ is —H and $R_6$ is —H or an aliphatic or substituted aliphatic group. More preferably, $R_1$ and $R_2$ are both a C3-C8 cycloalkyl group optionally substituted with at least one alkyl group; $R_3$ and $R_4$ are both an alkyl group; and $R_5$ is —H and $R_6$ is —H or methyl. Even more preferably, $R_1$ and $R_2$ are both cyclopropyl or 1-methylcyclopropyl; $R_3$ and $R_4$ are both an alkyl group, preferably methyl or ethyl; and $R_5$ is —H and $R_6$ is —H or methyl.

In specific embodiments, the bis(thiohydrazide amides) are represented by Structural Formula IV:

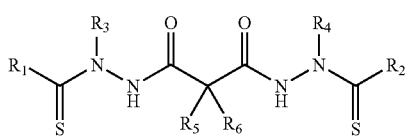

IV wherein: $R_1$ and $R_2$ are both phenyl, $R_3$ and $R_4$ are both methyl, and $R_5$ and $R_6$ are both —H; $R_1$ and $R_2$ are both phenyl, $R_3$ and $R_4$ are both ethyl, and $R_5$ and $R_6$ are both —H; $R_1$ and $R_2$ are both 4-cyanophenyl, $R_3$ and $R_4$ are both methyl, $R_5$ is methyl, and $R_6$ is —H; $R_1$ and $R_2$ are both 4-methoxyphenyl, $R_3$ and $R_4$ are both methyl, and $R_5$ and $R_6$ are both —H; $R_1$ and $R_2$ are both phenyl, $R_3$ and $R_4$ are both methyl, $R_5$ is methyl, and $R_6$ is —H; $R_1$ and $R_2$ are both phenyl, $R_3$ and $R_4$ are both ethyl, $R_5$ is methyl, and $R_6$ is —H; $R_1$ and $R_2$ are both 4-cyanophenyl, $R_3$ and $R_4$ are both methyl, and $R_5$ and $R_6$ are both —H; $R_1$ and $R_2$ are both 2,5-dimethoxyphenyl, $R_3$ and $R_4$ are both methyl, and $R_5$ and $R_6$ are both —H; $R_1$ and $R_2$ are both 2,5-dimethoxyphenyl, $R_3$ and $R_4$ are both methyl, $R_5$ is methyl, and $R_6$ is —H; $R_1$ and $R_2$ are both 3-cyanophenyl, $R_3$ and $R_4$ are both methyl, and $R_5$ and $R_6$ are both —H; $R_1$ and $R_2$ are both 3-fluorophenyl, $R_3$ and $R_4$ are both methyl, and $R_5$ and $R_6$ are both —H; $R_1$ and $R_2$ are both 4-chlorophenyl, $R_3$ and $R_4$ are both methyl, $R_5$ is methyl, and $R_6$ is —H; $R_1$ and $R_2$ are both 2-dimethoxyphenyl, $R_3$ and $R_4$ are both methyl, and $R_5$ and $R_6$ are both —H; $R_1$ and $R_2$ are both 3-methoxyphenyl, $R_3$ and $R_4$ are both methyl, and $R_5$ and $R_6$ are both —H; $R_1$ and $R_2$ are both 2,3-dimethoxyphenyl, $R_3$ and $R_4$ are both methyl, and $R_5$ and $R_6$ are both —H; $R_1$ and $R_2$ are both 2,3-dimethoxyphenyl, $R_3$ and $R_4$ are both methyl, $R_5$ is methyl, and $R_6$ is —H; $R_1$ and $R_2$ are both 2,5-difluorophenyl, $R_3$ and $R_4$ are both methyl, and $R_5$ and $R_6$ are both —H; $R_1$ and $R_2$ are both 2,5-difluorophenyl, $R_3$ and $R_4$ are both methyl, $R_5$ is methyl, and $R_6$ is —H; $R_1$ and $R_2$ are both 2,5-dichlorophenyl, $R_3$ and $R_4$ are both methyl, and $R_5$ and $R_6$ are both —H; $R_1$ and $R_2$ are both 2,5-dimethylphenyl, $R_3$ and $R_4$ are both methyl, and $R_5$ and $R_6$ are both —H; $R_1$ and $R_2$ are both 2,5-dimethoxyphenyl, $R_3$ and $R_4$ are both methyl, and $R_5$ and $R_6$ are both —H; $R_1$ and $R_2$ are both phenyl, $R_3$ and $R_4$ are both methyl, and $R_5$ and $R_6$ are both —H; $R_1$ and $R_2$ are both 2,5-dimethoxyphenyl, $R_3$ and $R_4$ are both methyl, $R_5$ is methyl, and $R_6$ is —H; $R_1$ and $R_2$ are both cyclopropyl, $R_3$ and $R_4$ are both methyl, and $R_5$ and $R_6$ are both —H; $R_1$ and $R_2$ are both cyclopropyl, $R_3$ and $R_4$ are both ethyl, and $R_5$ and $R_6$ are both —H; $R_1$ and $R_2$ are both cyclopropyl, $R_3$ and $R_4$ are both methyl, $R_5$ is methyl, and $R_6$ is —H; $R_1$ and $R_2$ are both 1-methylcyclopropyl, $R_3$ and $R_4$ are both methyl, and $R_5$ and $R_6$ are both —H; $R_1$ and $R_2$ are both 1-methylcyclopropyl, $R_3$ and $R_4$ are both methyl, $R_5$ is methyl and $R_6$ is —H; $R_1$ and $R_2$ are both 1-methylcyclopropyl, $R_3$ and $R_4$ are both methyl, $R_5$ is ethyl, and $R_6$ is —H; $R_1$ and $R_2$ are both 1-methylcyclopropyl, $R_3$ and $R_4$ are both methyl, $R_5$ is n-propyl, and $R_6$ is —H; $R_1$ and $R_2$ are both 1-methylcyclopropyl, $R_3$ and $R_4$ are both methyl, and $R_5$ and $R_6$ are both methyl; $R_1$ and $R_2$ are both 1-methylcyclopropyl, $R_3$ and $R_4$ are both ethyl, and $R_5$ and $R_6$ are both —H; $R_1$ and $R_2$ are both 1-methylcyclopropyl, $R_3$ is methyl, $R_4$ is ethyl, and $R_5$ and $R_6$ are both —H; $R_1$ and $R_2$ are both 2-methylcyclopropyl, $R_3$ and $R_4$ are both methyl, and $R_5$ and $R_6$ are both —H; $R_1$ and $R_2$ are both 2-phenylcyclopropyl, $R_3$ and $R_4$ are both methyl, and $R_5$ and $R_6$ are both —H; $R_1$ and $R_2$ are both 1-phenylcyclopropyl, $R_3$ and $R_4$ are both methyl, and $R_5$ and $R_6$ are both —H; $R_1$ and $R_2$ are both cyclobutyl, $R_3$ and $R_4$ are both methyl, and $R_5$ and $R_6$ are both —H; $R_1$ and $R_2$ are both cyclopentyl, $R_3$ and $R_4$ are both methyl, and $R_5$ and $R_6$ are both —H; $R_1$ and $R_2$ are both cyclohexyl, $R_3$ and $R_4$ are both methyl, and $R_5$ and $R_6$ are both —H; $R_1$ and $R_2$ are both cyclohexyl, $R_3$ and $R_4$ are both phenyl, and $R_5$ and $R_6$ are both —H; $R_1$ and $R_2$ are both methyl, $R_3$ and $R_4$ are both methyl, and $R_5$ and $R_6$ are both —H; $R_1$ and $R_2$ are both methyl, $R_3$ and $R_4$ are both t-butyl, and $R_5$ and $R_6$ are both —H; $R_1$ and $R_2$ are both methyl, $R_3$ and $R_4$ are both phenyl, and $R_5$ and $R_6$ are both —H; $R_1$ and $R_2$ are both t-butyl, $R_3$ and $R_4$ are both methyl, and $R_5$ and $R_6$ are both —H; $R_1$ and $R_2$ are ethyl, $R_3$ and $R_4$ are both methyl, and $R_5$ and $R_6$ are both —H; or $R_1$ and $R_2$ are both n-propyl, $R_3$ and $R_4$ are both methyl, and $R_5$ and $R_6$ are both —H.

In specific embodiments, the bis(thiohydrazide amides) are represented by Structural Formula V:

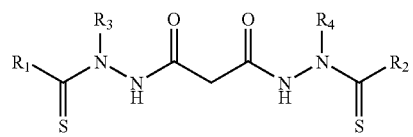

V wherein: $R_1$ and $R_2$ are both phenyl, and $R_3$ and $R_4$ are both o-$CH_3$-phenyl; $R_1$ and $R_2$ are both o-$CH_3C(O)O$-phenyl, and $R_3$ and $R_4$ are phenyl; $R_1$ and $R_2$ are both phenyl, and $R_3$ and $R_4$ are both methyl; $R_1$ and $R_2$ are both phenyl, and $R_3$ and $R_4$ are both ethyl; $R_1$ and $R_2$ are both phenyl, and $R_3$ and $R_4$ are both n-propyl; $R_1$ and $R_2$ are both p-cyanophenyl, and $R_3$ and $R_4$ are both methyl; $R_1$ and $R_2$ are both p-nitro phenyl, and $R_3$ and $R_4$ are both methyl; $R_1$ and $R_2$ are both 2,5-dimethoxyphenyl, and $R_3$ and $R_4$ are both methyl; $R_1$ and $R_2$ are both phenyl, and $R_3$ and $R_4$ are both n-butyl; $R_1$ and $R_2$ are both p-chlorophenyl, and $R_3$ and $R_4$ are both methyl; $R_1$ and $R_2$ are both 3-nitrophenyl, and $R_3$ and $R_4$ are both methyl; $R_1$ and $R_2$ are both 3-cyanophenyl, and $R_3$ and $R_4$ are both methyl; $R_1$ and $R_2$ are both 3-fluorophenyl, and $R_3$ and $R_4$ are both methyl; $R_1$ and $R_2$ are both 2-furanyl, and $R_3$ and $R_4$ are both phenyl; $R_1$ and $R_2$ are both 2-methoxyphenyl, and $R_3$ and $R_4$ are both methyl; $R_1$ and $R_2$ are both 3-methoxyphenyl, and $R_3$ and $R_4$ are both methyl; $R_1$ and $R_2$ are both 2,3-dimethoxyphenyl, and $R_3$ and $R_4$ are both methyl; $R_1$ and $R_2$ are both 2-methoxy-5-chlorophenyl, and $R_3$ and $R_4$ are both ethyl; $R_1$ and $R_2$ are both 2,5-difluorophenyl, and $R_3$ and $R_4$ are both methyl; $R_1$ and $R_2$ are both 2,5-dichlorophenyl, and $R_3$ and $R_4$ are both methyl; $R_1$ and $R_2$ are both 2,5-dimethylphenyl, and $R_3$ and $R_4$ are both methyl; $R_1$ and $R_2$ are both 2-methoxy-5-chlorophenyl, and $R_3$ and $R_4$ are both methyl; $R_1$ and $R_2$ are both 3,6-dimethoxyphenyl, and $R_3$ and $R_4$ are both methyl; $R_1$ and $R_2$ are both phenyl, and $R_3$ and $R_4$ are both 2-ethylphenyl; $R_1$ and $R_2$ are both 2-methyl-5-pyridyl, and $R_3$ and $R_4$ are both methyl; or $R_1$ is phenyl; $R_2$ is 2,5-dimethoxyphenyl, and $R_3$ and $R_4$ are both methyl; $R_1$ and $R_2$ are both methyl, and $R_3$ and $R_4$ are both p-$CF_3$-phenyl; $R_1$ and $R_2$ are both methyl, and $R_3$ and $R_4$ are both o-$CH_3$-phenyl; $R_1$ and $R_2$ are both —$(CH_2)_3COOH$; and $R_3$ and $R_4$ are both phenyl; $R_1$ and $R_2$ are both represented by the following structural formula:

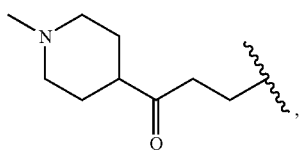

and $R_3$ and $R_4$ are both phenyl; $R_1$ and $R_2$ are both n-butyl, and $R_3$ and $R_4$ are both phenyl; $R_1$ and $R_2$ are both n-pentyl, $R_3$ and $R_4$ are both phenyl; $R_1$ and $R_2$ are both methyl, and $R_3$ and $R_4$ are both 2-pyridyl; $R_1$ and $R_2$ are both cyclohexyl, and $R_3$ and $R_4$ are both phenyl; $R_1$ and $R_2$ are both methyl, and $R_3$ and $R_4$ are both 2-ethylphenyl; $R_1$ and $R_2$ are both methyl, and $R_3$ and $R_4$ are both 2,6-dichlorophenyl; $R_1$-$R_4$ are all methyl; $R_1$ and $R_2$ are both methyl, and $R_3$ and $R_4$ are both t-butyl; $R_1$ and $R_2$ are both ethyl, and $R_3$ and $R_4$ are both methyl; $R_1$ and $R_2$ are both t-butyl, and $R_3$ and $R_4$ are both methyl; $R_1$ and $R_2$ are both cyclopropyl, and $R_3$ and $R_4$ are both methyl; $R_1$ and $R_2$ are both cyclopropyl, and $R_3$ and $R_4$ are both ethyl; $R_1$ and $R_2$ are both 1-methylcyclopropyl, and $R_3$ and $R_4$ are both methyl; $R_1$ and $R_2$ are both 2-methylcyclopropyl, and $R_3$ and $R_4$ are both methyl; $R_1$ and $R_2$ are both 1-phenylcyclopropyl, and $R_3$ and $R_4$ are both methyl; $R_1$ and $R_2$ are both 2-phenylcyclopropyl, and $R_3$ and $R_4$ are both methyl; $R_1$ and $R_2$ are both cyclobutyl, and $R_3$ and $R_4$ are both methyl; $R_1$ and $R_2$ are both cyclopentyl, and $R_3$ and $R_4$ are both methyl; $R_1$ is cyclopropyl, $R_2$ is phenyl, and $R_3$ and $R_4$ are both methyl.

Preferred examples of bis(thiohydrazide amides) include Compounds (1)-(18) and pharmaceutically acceptable salts and solvates thereof:

Compound (1)
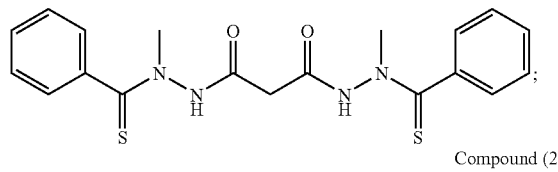

Compound (2)
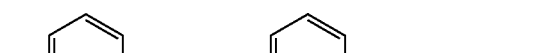

Compound (3)
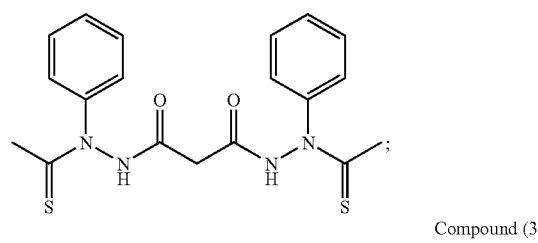

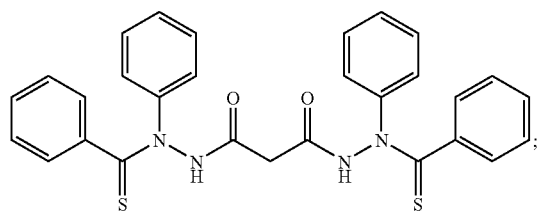

Compound (4)
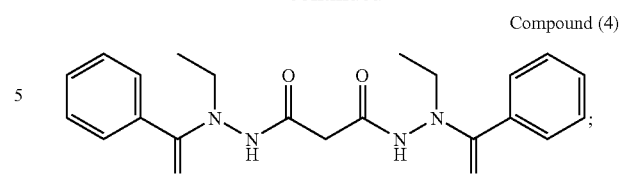

Compound (5)
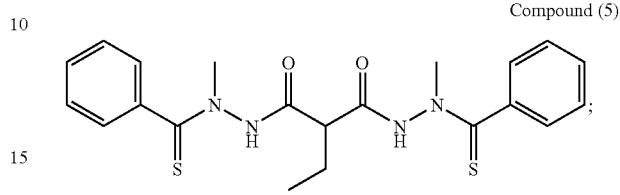

Compound (6)
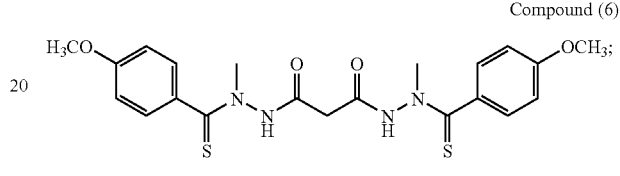

Compound (7)
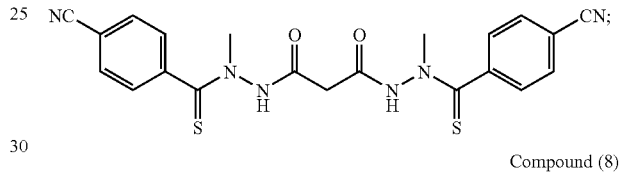

Compound (8)
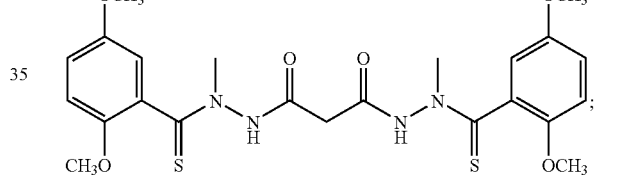

Compound (9)
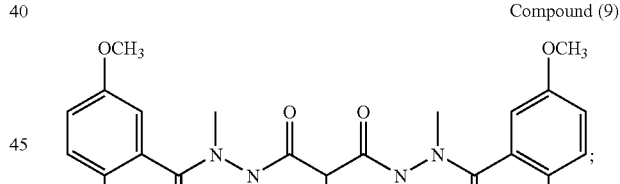

Compound (10)
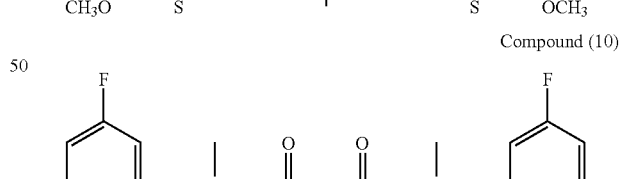

Compound (11)
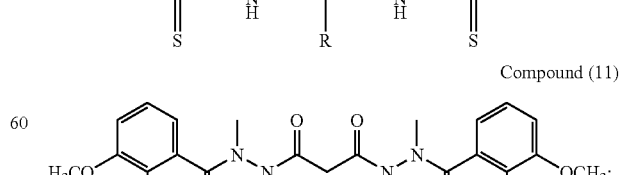

-continued

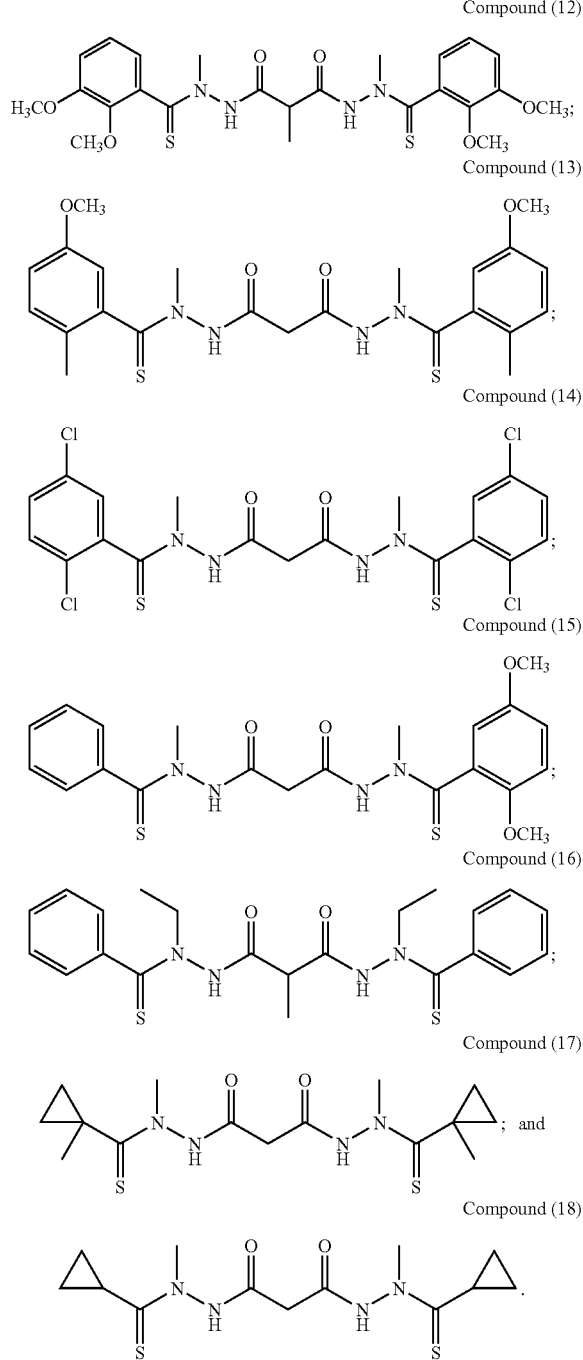

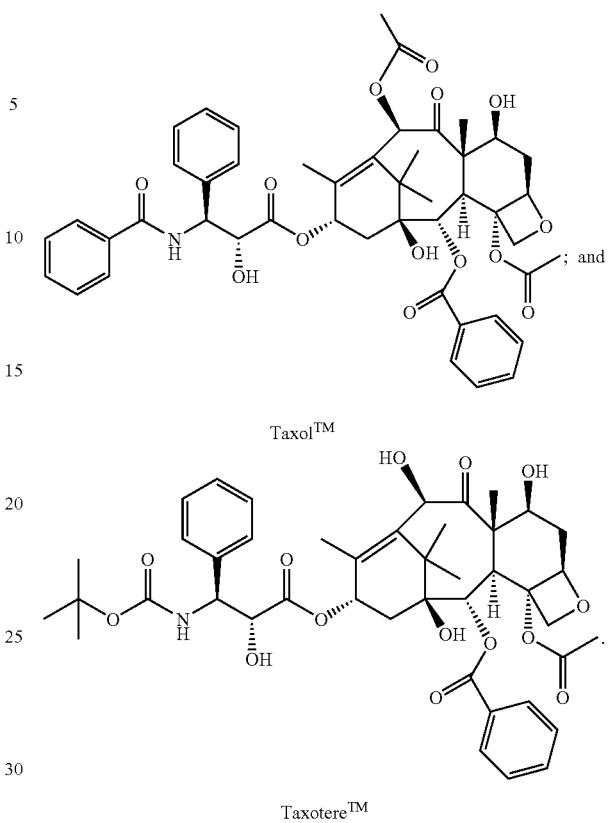

Particular examples of bis(thiohydrazide amides) include Compounds (1), (17), and (18) and pharmaceutically acceptable salts and solvates thereof.

The taxanes employed in the disclosed invention include Taxol™ and Taxol™ analogs. Taxol™ or "paclitaxel" is a well-known anti-cancer drug which can act by enhancing and stabilizing microtubule formation. Thus, the term "Taxol™ analog" is defined herein to mean a compound which has the basic Taxol™ skeleton and which stabilizes microtubule formation. Many analogs of Taxol™ are known, including Taxotere™, also referred to as "docetaxol". Taxol™ and Taxotere™ have the respective structural formulas:

The taxanes employed in the disclosed invention have the basic taxane skeleton as a common structure feature shown below in Structural Formula VI:

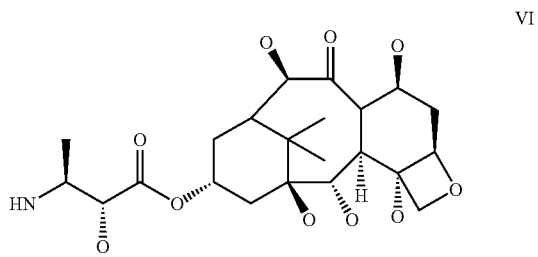

Double bonds have been omitted from the cyclohexane rings in the taxane skeleton represented by Structural Formula VI. It is to be understood that the basic taxane skeleton can include zero or one double bond in one or both cyclohexane rings, as indicated in the Taxol™ analogs and Structural Formulas VII and VIII below. A number of atoms have also been omitted from Structural Formula VI to indicate sites in which structural variation commonly occurs among Taxol™ analogs.

A wide variety of substituents can decorate the taxane skeleton without adversely affecting biological activity. Also, zero, one or both of the cyclohexane rings of a Taxol™ analog can have a double bond at the indicated positions. For example, substitution on the taxane skeleton with simply an oxygen atom indicates that hydroxyl, acyl, alkoxy or other oxygen-bearing substituent is commonly found at the site. It is to be understood that these and other substitutions on the taxane skeleton can be made without losing the ability to enhance and stabilize microtubule formation. Thus, the term "Taxol™ analog" is defined herein to mean a compound which has the basic Taxol™ skeleton and which stabilizes microtubule formation. The term taxane is defined herein to include compounds such as Taxol™ and the "Taxol™ analogs" described herein, or a pharmaceutically acceptable salt or solvate thereof.

Typically, the taxanes employed in the disclosed invention are represented by Structural Formula VII or VIII:

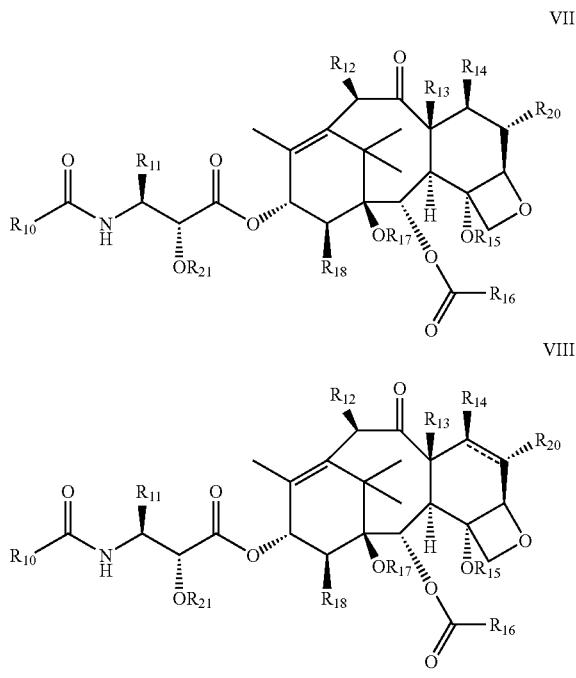

$R_{10}$ is an optionally substituted lower alkyl group, an optionally substituted phenyl group, —$SR_{19}$, —$NHR_{19}$ or —$OR_{19}$.

$R_{11}$ is an optionally substituted lower alkyl group, an optionally substituted aryl group.

$R_{12}$ is —H, —OH, lower alkyl, substituted lower alkyl, lower alkoxy, substituted lower alkoxy, —O—C(O)-(lower alkyl), —O—C(O)-(substituted lower alkyl), —O—CH$_2$—O-(lower alkyl)-S—CH$_2$—O-(lower alkyl).

$R_{13}$ is —H, —CH$_3$, or, taken together with $R_{14}$, —CH$_2$—.

$R_{14}$ is —H, —OH, lower alkoxy, —O—C(O)-(lower alkyl), substituted lower alkoxy, —O—C(O)-(substituted lower alkyl), —O—CH$_2$—O—P(O)(OH)$_2$, —O—CH$_2$—O-(lower alkyl), —O—CH$_2$—S-(lower alkyl) or, taken together with $R_{20}$, a double bond.

$R_{15}$—H, lower acyl, lower alkyl, substituted lower alkyl, alkoxymethyl, alkthiomethyl, —OC(O)—O(lower alkyl), —OC(O)—O(substituted lower alkyl), —OC(O)—NH (lower alkyl) or —OC(O)—NH(substituted lower allyl).

$R_{16}$ is phenyl or substituted phenyl.

$R_{17}$ is —H, lower acyl, substituted lower acyl, lower alkyl, substituted, lower alkyl, (lower alkoxy)methyl or (lower alkyl)thiomethyl.

$R_{18}$—H, —CH$_3$ or, taken together with $R_{17}$ and the carbon atoms to which $R_{17}$ and $R_{18}$ are bonded, a five or six membered a non-aromatic heterocyclic ring.

$R_{19}$ is an optionally substituted lower alkyl group, an optionally substituted phenyl group.

$R_{20}$ is —H or a halogen.

$R_{21}$ is —H, lower alkyl, substituted lower alkyl, lower acyl or substituted lower acyl.

Preferably, the variables in Structural Formulas VII and VIII are defined as follows: $R_{10}$ is phenyl, tert-butoxy, —S—CH$_2$—CH—(CH$_3$)$_2$, —S—CH(CH$_3$)$_3$, —S—(CH$_2$)$_3$CH$_3$, —O—CH(CH$_3$)$_3$, —NH—CH(CH$_3$)$_3$, —CH═C(CH$_3$)$_2$ or para-chlorophenyl; $R_{11}$ is phenyl, (CH$_3$)$_2$CHCH$_2$—, -2-furanyl, cyclopropyl or para-toluoyl; $R_{12}$ is —H, —OH, CH$_3$CO— or —(CH$_2$)$_2$—N-morpholino; $R_{13}$ is methyl, or, $R_{13}$ and $R_{14}$, taken together, are —CH$_2$—;

$R_{14}$ is —H, —CH$_2$SCH$_3$ or —CH$_2$—O—P(O)(OH)$_2$; $R_{15}$ is CH$_3$CO—;

$R_{16}$ is phenyl; $R_{17}$—H, or, $R_{17}$ and $R_{18}$, taken together, are —O—CO—O—;

$R_{18}$ is —H; $R_{20}$ is —H or —F; and $R_{21}$ is —H, —C(O)—CHBr—(CH$_2$)$_{13}$—CH$_3$ or —C(O)—(CH$_2$)$_{14}$—CH$_3$; —C(O)—CH$_2$—CH(OH)—COOH, —C(O)—CH$_2$—O—C(O)—CH$_2$CH(NH$_2$)—CONH$_2$, —C(O)—CH$_2$—O—CH$_2$CH$_2$OCH$_3$ or —C(O)—O—C(O)—CH$_2$CH$_3$.

Specific examples of Taxol™ analogs include the following compounds:

Taxol™ analog 1

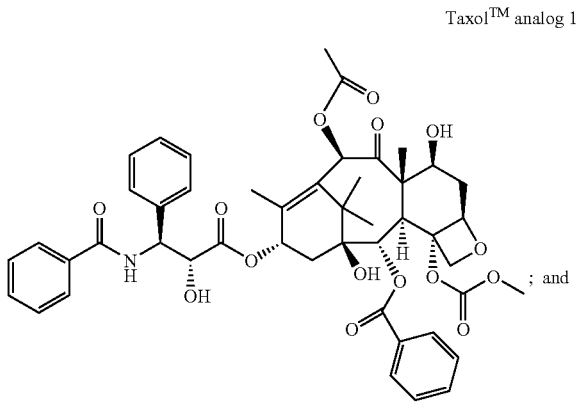

; and

Taxol™ analog 2

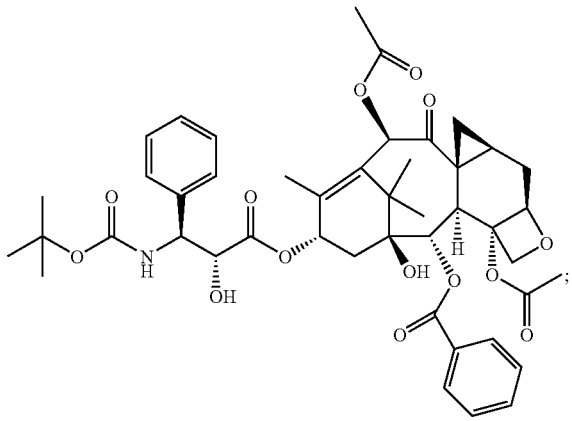

;

Taxol™ analog 3
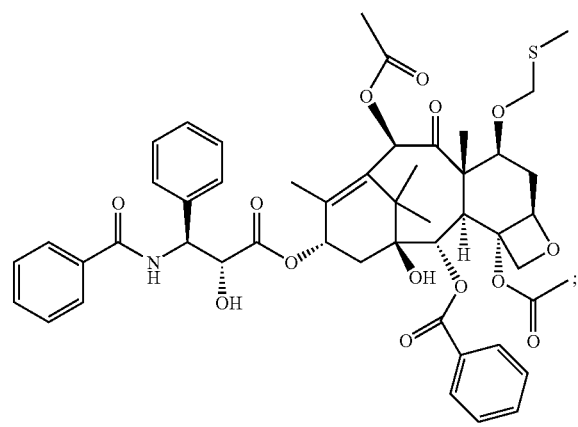
Taxol™ analog 4
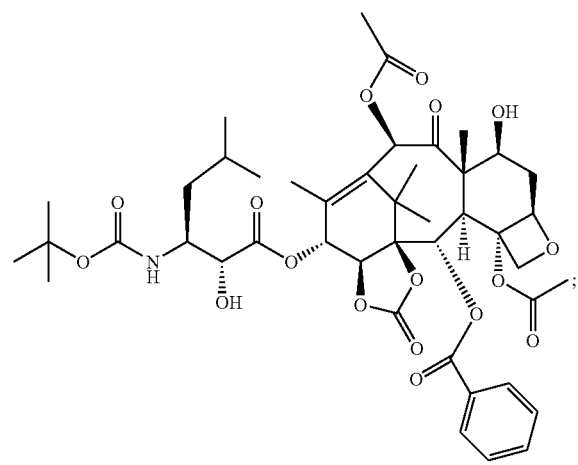
Taxol™ analog 5
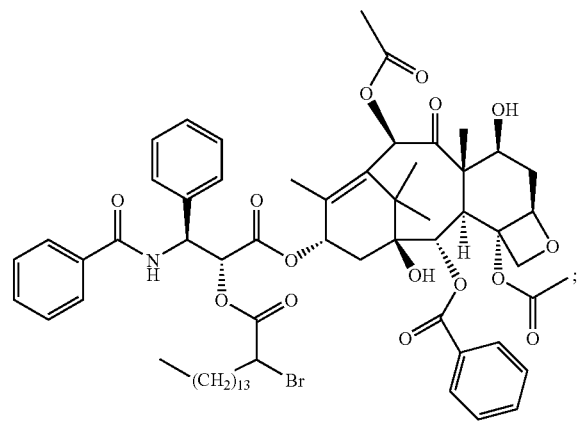
Taxol™ analog 6
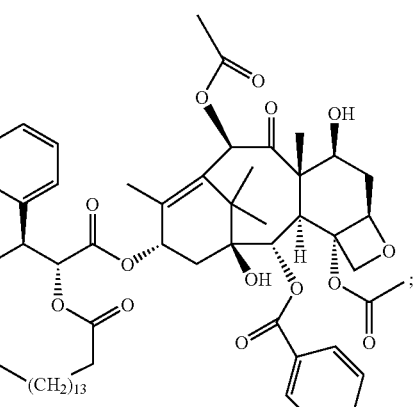
Taxol™ analog 7
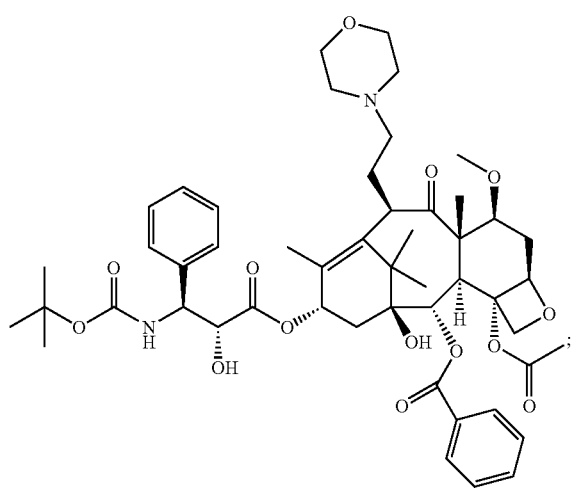
Taxol™ analog 8
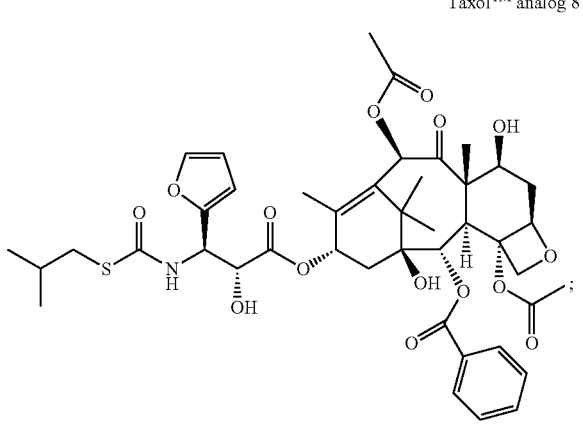

Taxol™ analog 9
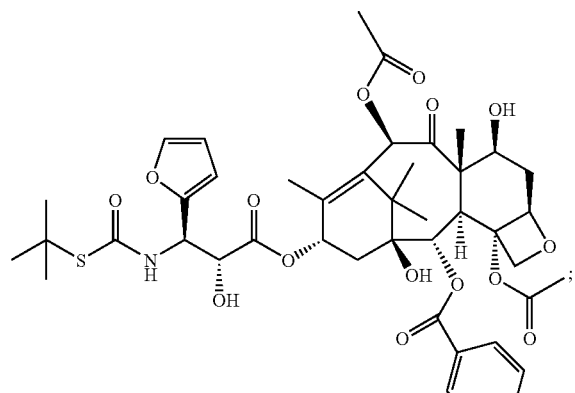
Taxol™ analog 10
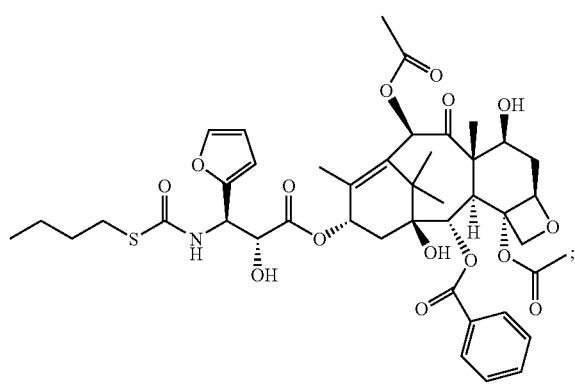
Taxol™ analog 11
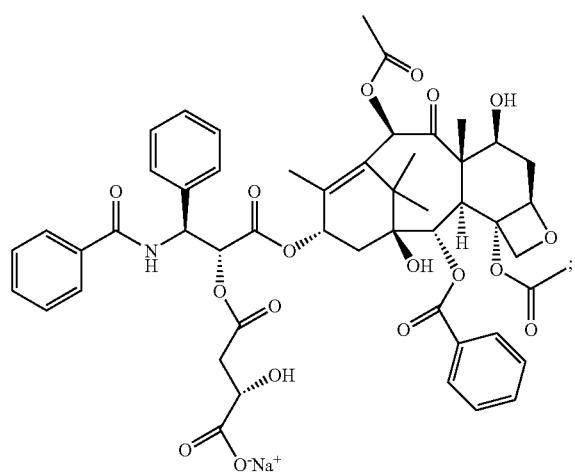
Taxol™ analog 12
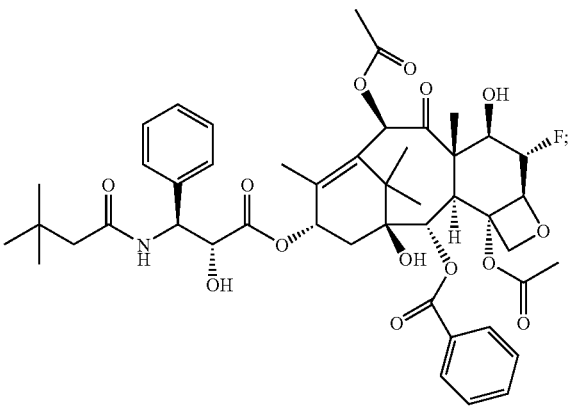
Taxol™ analog 13
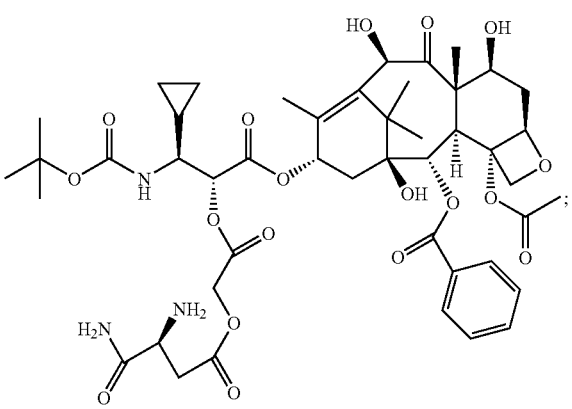
Taxol™ analog 14
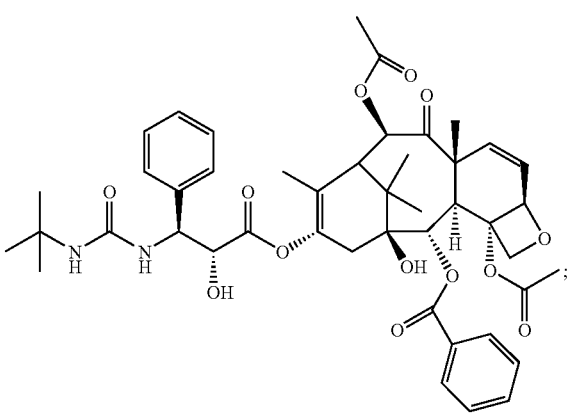

Taxol™ analog 15
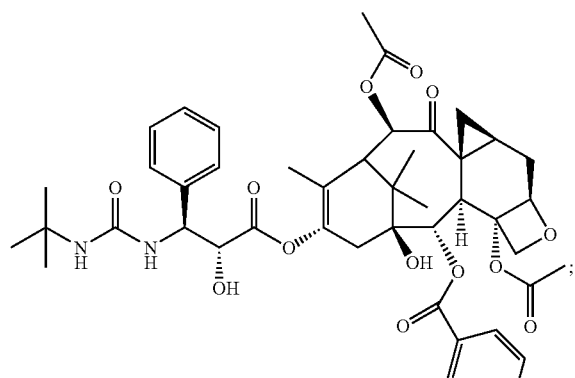
Taxol™ analog 18
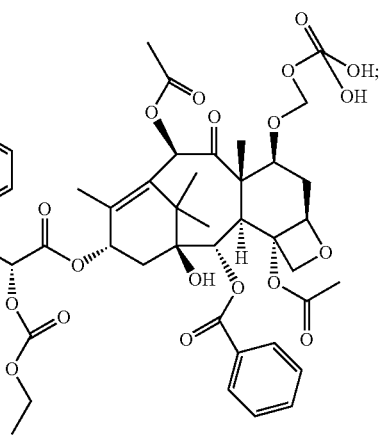
Taxol™ analog 16
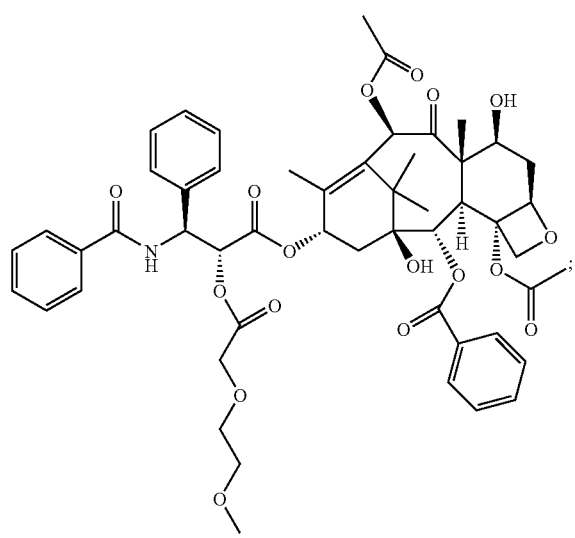
Taxol™ analog 19
Taxol™ analog 17
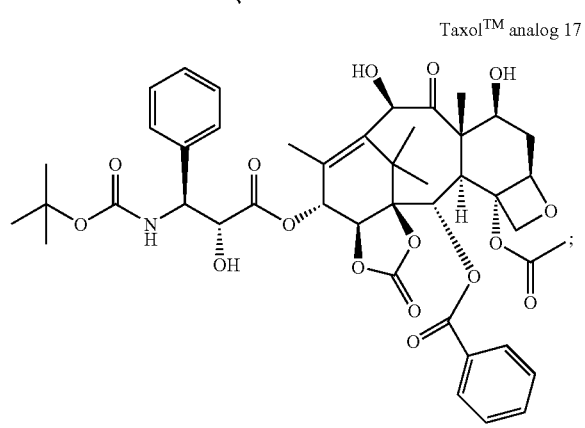
Taxol™ analog 20

-continued

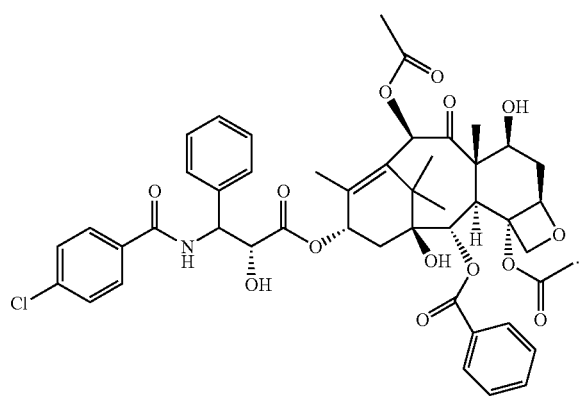

Taxol™ analog 21

A Taxol™ analog can also be bonded to or be pendent from a pharmaceutically acceptable polymer, such as a polyacrylamide. One example of a polymer of this type is Taxol™ analog 22, below, which has the structure of a polymer comprising a taxol analog group pendent from the polymer backbone. The polymer is a terpolymer of the three monomer units shown. The term "Taxol™ analog", as it is used herein, includes such polymers.

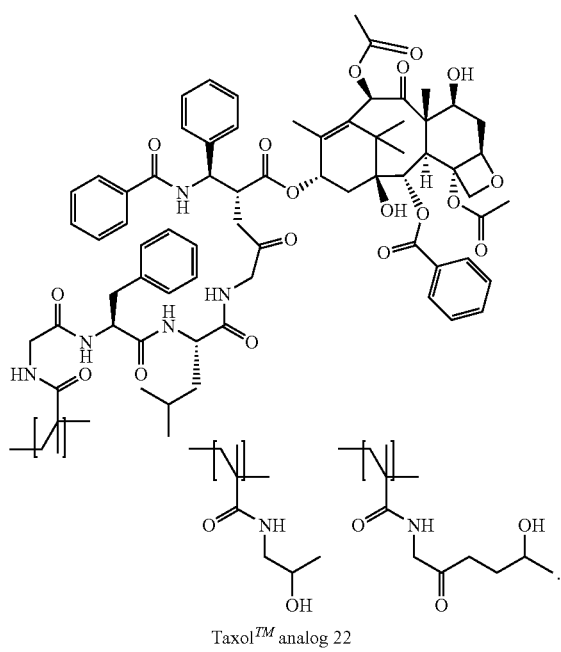

Taxol™ analog 22

A "straight chained hydrocarbyl group" is an alkylene group, i.e., —(CH$_2$)$_y$—, with one, or more (preferably one) internal methylene groups optionally replaced with a linkage group. y is a positive integer (e.g., between 1 and 10), preferably between 1 and 6 and more preferably 1 or 2. A "linkage group" refers to a functional group which replaces a methylene in a straight chained hydrocarbyl. Examples of suitable linkage groups include a ketone (—C(O)—), alkene, alkyne, phenylene, ether (—O—), thioether (—S—), or amine (—N(R$^a$)—), wherein R$^a$ is defined below. A preferred linkage group is —C(R$_5$R$_6$)—, wherein R$_5$ and R$_6$ are defined above. Suitable substituents for an alkylene group and a hydrocarbyl group are those which do not substantially interfere with the anti-cancer activity of the bis(thiohydrazide) amides and taxanes. R$_5$ and R$_6$ are preferred substituents for an alkylene or hydrocarbyl group represented by Y.

An aliphatic group is a straight chained, branched or cyclic non-aromatic hydrocarbon which is completely saturated or which contains one or more units of unsaturation. Typically, a straight chained or branched aliphatic group has from 1 to about 20 carbon atoms, preferably from 1 to about 10, and a cyclic aliphatic group has from 3 to about 10 carbon atoms, preferably from 3 to about 8. An aliphatic group is preferably a straight chained or branched alkyl group, e.g., methyl, ethyl, n-propyl, iso-propyl, n-butyl, sec-butyl, tert-butyl, pentyl, hexyl, pentyl or octyl, or a cycloalkyl group with 3 to about 8 carbon atoms. A C1-C20 straight chained or branched alkyl group or a C3-C8 cyclic alkyl group is also referred to as a "lower alkyl" group.

The term "aromatic group" may be used interchangeably with "aryl," "aryl ring," "aromatic ring," "aryl group" and "aromatic group." Aromatic groups include carbocyclic aromatic groups such as phenyl, naphthyl, and anthracyl, and heteroaryl groups such as imidazolyl, thienyl, furanyl, pyridyl, pyrimidyl, pyranyl, pyrazolyl, pyrroyl, pyrazinyl, thiazole, oxazolyl, and tetrazole. The term "heteroaryl group" may be used interchangeably with "heteroaryl," "heteroaryl ring," "heteroaromatic ring" and "heteroaromatic group." The term "heteroaryl," as used herein, means a mono- or multi-cyclic aromatic heterocycle which comprise at least one heteroatom such as nitrogen, sulfur and oxygen, but may include 1, 2, 3 or 4 heteroatoms per ring. Aromatic groups also include fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazole, benzooxazole, benzimidazole, quinolinyl, isoquinolinyl and isoindolyl.

The term "arylene" refers to an aryl group which is connected to the remainder of the molecule by two other bonds. By way of example, the structure of a 1,4-phenylene group is shown below:

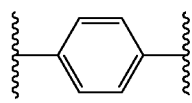

Substituents for an arylene group are as described below for an aryl group.

Non-aromatic heterocyclic rings are non-aromatic rings which include one or more heteroatoms such as nitrogen, oxygen or sulfur in the ring. The ring can be five, six, seven or eight-membered. Examples include tetrahydrofuranyl, tetrahydrothiophenyl, morpholino, thiomorpholino, pyrrolidinyl, piperazinyl, piperidinyl, and thiazolidinyl.

Suitable substituents on an aliphatic group (including an alkylene group), non-aromatic heterocyclic group, benzylic or aryl group (carbocyclic and heteroaryl) are those which do not substantially interfere with the anti-cancer activity of the bis(thiohydrazide) amides and taxanes. A substituent substantially interferes with anti-cancer activity when the anti-cancer activity is reduced by more than about 50% in a compound with the substituent compared with a compound without the substituent. Examples of suitable substituents include —R$^a$, —OH, —Br, —Cl, —I, —F, —OR$^a$, —O—COR$^a$, COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NR$^c$COR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$H—C(=NH)—NH$_2$, —NR$^d$—C(=NH)—NHR$^a$, —NR$^d$—C(=NH)—N(R$^a$R$^b$), —NR$^d$—C(=NR$^c$)—NH$_2$, —NR$^d$—C(=NR$^c$)—NHR$^a$, —NR$^d$—C(=NR$^c$)—N(R$^a$R$^b$), —NHNH$_2$, —NHNHR$^a$, —NHR$^a$R$^b$, —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SR$^a$, —S(O)R$^a$, —S(O)$_2$R$^a$. R$^a$R$^d$ are each independently an alkyl group, aromatic group, non-aromatic heterocyclic group or —N(R$^a$R$^b$), taken together, form an optionally substituted non-aromatic heterocyclic group. The alkyl, aromatic and non-aromatic heterocyclic group represented by R$^a$-R$^d$ and the non-aromatic heterocyclic group represented by —N(R$^a$R$^b$) are each optionally and independently substituted with one or more groups represented by R#.

R$^\#$ is R$^+$, —OR$^+$, —O(haloalkyl), —SR$^+$, —NO$_2$, —CN, —NCS, —N(R$^+$)$_2$, —NHCO$_2$R$^+$, —NHC(O)R$^+$, —NHNHC(O)R$^+$, —NHC(O)N(R$^+$)$_2$, —NHNHC(O)N(R$^+$)$_2$, —NHNHCO$_2$R$^+$, —C(O)C(O)R$^+$, —C(O)CH$_2$C(O)R$^+$, —CO$_2$R$^+$, —C(O)R$^+$, —C(O)N(R$^+$)$_2$, —OC(O)R$^+$, —OC(O)N(R$^+$)$_2$, —S(O)$_2$R$^+$, —SO$_2$N(R$^+$)$_2$, —S(O)R$^+$, —NHSO$_2$N(R$^+$)$_2$, —NHSO$_2$R$^+$, —C(=S)N(R$^+$)$_2$, or —C(=NH)—N(R$^+$)$_2$.

R$^+$ is —H, a C1-C4 alkyl group, a monocyclic heteroaryl group, a non-aromatic heterocyclic group or a phenyl group optionally substituted with alkyl, haloalkyl, alkoxy, haloalkoxy, halo, —CN, —NO$_2$, amine, alkylamine or dialkylamine. Optionally, the group —N(R$^+$)$_2$ is a non-aromatic heterocyclic group, provided that non-aromatic heterocyclic groups represented by R$^+$ and —N(R$^+$)$_2$ that comprise a secondary ring amine are optionally acylated or alkylated.

Preferred substituents for a phenyl group, including phenyl groups represented by R$_1$-R$_4$, include C1-C4 alkyl, C1-C4 alkoxy, C1-C4 haloalkyl, C1-C4 haloalkoxy, phenyl, benzyl, pyridyl, —OH, —NH$_2$, —F, —Cl, —Br, —I, —NO$_2$ or —CN.

Preferred substituents for an aliphatic group, including aliphatic groups represented by R$_1$-R$_4$, include C1-C4 alkyl, C1-C4 alkoxy, C1-C4 haloalkyl, C1-C4 haloalkoxy, phenyl, benzyl, pyridyl, —OH, —NH$_2$, —F, —Cl, —Br, —I, —NO$_2$ or —CN.

Preferred substituents for a cycloalkyl group, including cycloalkyl groups represented by R$_1$ and R$_2$, are alkyl groups, such as a methyl or ethyl groups.

Also included in the present invention are pharmaceutically acceptable salts of the bis(thiohydrazide) amides and taxanes employed herein. These compounds can have one or more sufficiently acidic protons that can react with a suitable organic or inorganic base to form a base addition salt. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Such bases useful in preparing the salts of this invention thus include sodium hydroxide, potassium hydroxide, ammonium hydroxide, potassium carbonate, and the like.

For example, pharmaceutically acceptable salts of bis(thiohydrazide) amides and taxanes employed herein (e.g., those represented by Structural Formulas I-VI, Compounds 1-18, and Taxol™ analogs 1-22) are those formed by the reaction of the compound with one equivalent of a suitable base to form a monovalent salt (i.e., the compound has single negative charge that is balanced by a pharmaceutically acceptable counter cation, e.g., a monovalent cation) or with two equivalents of a suitable base to form a divalent salt (e.g., the compound has a two-electron negative charge that is balanced by two pharmaceutically acceptable counter cations, e.g., two pharmaceutically acceptable monovalent cations or a single pharmaceutically acceptable divalent cation). Divalent salts of the bis(thiohydrazide amides) are preferred. "Pharmaceutically acceptable" means that the cation is suitable for administration to a subject. Examples include Li$^+$, Na$^+$, K$^+$, Mg$^+$, Ca$^{2+}$ and NR$_4^+$, wherein each R is independently hydrogen, an optionally substituted aliphatic group (e.g., a hydroxyalkyl group, aminoalkyl group or ammoniumalkyl group) or optionally substituted aryl group, or two R groups, taken together, form an optionally substituted non-aromatic heterocyclic ring optionally fused to an aromatic ring. Generally, the pharmaceutically acceptable cation is Li$^+$, Na$^+$, K$^+$, NH$_3$(C$_2$H$_5$OH)$^+$ or N(CH$_3$)$_3$(C$_2$H$_5$OH)$^+$, and more typically, the salt is a disodium or dipotassium salt, preferably the disodium salt.

Bis(thiohydrazide) amides and taxanes employed herein having a sufficiently basic group, such as an amine can react with an organic or inorganic acid to form an acid addition salt. Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Particular salts of the bis(thiohydrazide amide) compounds described herein can be prepared according to methods described in copending, co-owned Patent Application Ser. No. 60/582,596, filed Jun. 23, 2004.

The neutral bis(thiohydrazide) amides can be prepared according to methods described in U.S. Pat. Nos. 6,800,660, and 6,762,204, both entitled "Synthesis of Taxol Enhancers" and also according to methods described in the co-pending and co-owned U.S. patent application Ser. Nos. 10/345,885 filed Jan. 15, 2003, and 10/758,589, Jan. 15, 2004. The entire teachings of each document referred to in this application is expressly incorporated herein by reference.

It will also be understood that certain compounds employed in the invention may be obtained as different stereoisomers (e.g., diastereomers and enantiomers) and that the invention includes all isomeric forms and racemic mixtures of the disclosed compounds and methods of treating a subject with both pure isomers and mixtures thereof, including racemic mixtures. Stereoisomers can be separated and isolated using any suitable method, such as chromatography.

As used herein, a "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The bis(thiohydrazide) amides and taxanes employed herein can be administered to a subject by any conventional method of drug administration for treatment of cancerous disorders, for example, orally in capsules, suspensions or tablets or by parenteral administration. Parenteral administration can include, for example, systemic administration, such as by intramuscular, intravenous, subcutaneous, or intraperitoneal injection. In specific embodiments, oral, parenteral, or local administration are preferred modes of administration for treatment of cancer. Preferably, the mode of administration is intravenous.

An effective amount of a bis(thio-hydrazide) amide or a taxane anticancer compound is a quantity in which anti-cancer effects are normally achieved. With respect to a particular compound in the method (e.g., the bis(thio-hydrazide) amide or the taxane anticancer compound), an "effective amount" is the quantity in which a greater anti-cancer effect is achieved when the particular compound is co-administered with the other compounds in the method compared with when the particular compound is administered alone. The compounds of the method can be co-administered to the subject as part of the same pharmaceutical composition or, alternatively, as separate pharmaceutical compositions. When administered as separate pharmaceutical compositions, the compounds of the method can be administered simultaneously or at different times, provided that the enhancing effect of the compounds in combination is retained.

As used herein, "treating a subject with a cancer," or similar terms, includes achieving, partially or substantially, one or more of the following: arresting the growth or spread of a cancer, reducing the extent of a cancer (e.g., reducing size of a tumor or reducing the number of affected sites), inhibiting the growth rate of a cancer, and ameliorating or improving a clinical symptom or indicator associated with a cancer (such as tissue or serum components).

In various embodiments, cancer can include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia, and heavy chain disease.

In some embodiments, cancer can include leukemias e.g., acute and/or chronic leukemias, e.g., lymphocytic leukemia (e.g., as exemplified by the p388 (murine) cell line), large granular lymphocytic leukemia, and lymphoblastic leukemia; T-cell leukemias, e.g., T-cell leukemia (e.g., as exemplified by the CEM, Jurkat, and HSB-2 (acute), YAC-1 (murine) cell lines), T-lymphocytic leukemia, and T-lymphoblastic leukemia; B cell leukemia (e.g., as exemplified by the SB (acute) cell line), and B-lymphocytic leukemia; mixed cell leukemias, e.g., B and T cell leukemia and B and T lymphocytic leukemia; myeloid leukemias, e.g., granulocytic leukemia, myelocytic leukemia (e.g., as exemplified by the HL-60 (promyelocyte) cell line), and myelogenous leukemia (e.g., as exemplified by the K562 (chronic) cell line); neutrophilic leukemia; eosinophilic leukemia; monocytic leukemia (e.g., as exemplified by the THP-1 (acute) cell line); myelomonocytic leukemia; Naegeli-type myeloid leukemia; and nonlymphocytic leukemia. Other examples of leukemias are described in Chapter 60 of *The Chemotherapy Sourcebook*, Michael C. Perry Ed., Williams & Williams (1992) and Section 36 of *Holland Frie Cancer Medicine* 5th Ed., Bast et al. Eds., B.C. Decker Inc. (2000). The entire teachings of the preceding references are incorporated herein by reference.

In certain embodiments, cancer can include non-solid tumors such as multiple myeloma, T-leukemia (e.g., as exemplified by Jurkat and CEM cell lines); B-leukemia (e.g., as exemplified by the SB cell line); promyelocytes (e.g., as exemplified by the HL-60 cell line); uterine sarcoma (e.g., as exemplified by the MES-SA cell line); monocytic leukemia (e.g., as exemplified by the THP-1 (acute) cell line); and lymphoma (e.g., as exemplified by the U937 cell line).

In some embodiments, cancer can include colon cancer, pancreatic cancer, melanoma, renal cancer, sarcoma, breast cancer, ovarian cancer, lung cancer, stomach cancer, bladder cancer and cervical cancer.

In some embodiments, the disclosed methods can be particularly effective at treating subjects whose cancer has become "multi-drug resistant". A cancer which initially responded to an anti-cancer drug becomes resistant to the anti-cancer drug when the anti-cancer drug is no longer effective in treating the subject with the cancer. For example, many tumors can initially respond to treatment with an anti-cancer drug by decreasing in size or even going into remission, only to develop resistance to the drug. Drug resistant tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant". For example, it is common for cancers to become resistant to three or more anti-cancer agents, often five or more anti-cancer agents and at times ten or more anti-cancer agents.

The bis(thiohydrazide) amides and taxanes employed herein can be administered to the subject in conjunction with an acceptable pharmaceutical carrier or diluent as part of a pharmaceutical composition for treatment cancer therapy. Formulation of the compound to be administered will vary according to the route of administration selected (e.g., solution, emulsion, capsule, and the like). Suitable pharmaceutically acceptable carriers may contain inert ingredients which do not unduly inhibit the biological activity of the compounds. The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed, such as those described in Remington's Pharmaceutical Sciences, ibid. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

In certain embodiments, one or more compounds of the invention and one or more other the therapies (e.g., prophylactic or therapeutic agents) are cyclically administered. Cycling therapy involves the administration of a first therapy (e.g., a first prophylactic or therapeutic agents) for a period of time, followed by the administration of a second therapy (e.g., a second prophylactic or therapeutic agents) for a period of time, followed by the administration of a third therapy (e.g., a third prophylactic or therapeutic agents) for a period of time and so forth, and repeating this sequential administration, i.e., the cycle in order to reduce the development of resistance to one of the agents, to avoid or reduce the side effects of one of the agents, and/or to improve the efficacy of the treatment.

In various embodiments, the methods herein can include administration prior to or concurrently with the bis(thiohydrazide) amide/taxane combination, agents that can reduce acute irritation or allergic reaction to administration, e.g., an anti-inflammatory such as Decadron® (dexamethasone, e.g., 10 mg intravenously), an antihistamine such as Benadryl® (diphenhydramine, e.g., 50 mg intravenously), an antacid such as Zantac® (ranitidine hydrochloride, e.g., 50 mg intravenously), and the like.

EXEMPLIFICATION

Example 1

Measurement of Heat Shock Protein 70 (Hsp70)

Plasma Hsp70 was measured by a sandwich ELISA kit (Stressgen Bioreagents Victoria, British Columbia, CANADA) according to a modified protocol in house. In brief, Hsp70 in plasma specimens and serial concentrations of Hsp70 standard were captured onto 96-well plate on which anti-Hsp70 antibody was coated. Then captured Hsp70 was detected with a biotinylated anti-Hsp70 antibody followed by incubation with europium-conjugated streptavidin. After each incubation unbound materials were removed by washing. Finally, antibody-Hsp70 complex was measured by time resolved fluorometry of europium. Concentration of Hsp70 was calculated from a standard curve.

Example 2

Measurement of Natural Killer Cell Cytotoxic Activity

The following procedure can be employed to assay NK cell activity in a subject. The procedure is adapted from Kantakamalakul W, Jaroenpool J, Pattanapanyasat K. A novel enhanced green fluorescent protein (EGFP)-K562 flow cytometric method for measuring natural killer (NK) cell cytotoxic activity. J Immunol Methods. 2003 Jan. 15; 272:189-197, the entire teachings of which are incorporated herein by reference.

Materials and methods: Human erythroleukaemic cell line, K562, was obtained from American Type Culture Collection (CCL-243, American Type Culture Collection, Manassas, Va.), and cultured in RPMI-1640 medium (Cat# 11875-093Gibco Invitrogen Corp, Carlsbad, Calif.) supplemented with 10% heat inactivated fetal calf serum (Gibco), 2 mM L-glutamin, 100 µg/ml streptomycin and 100 IU/ml penicillin at 37° C. with 5% $CO_2$. K562 cells were transduced with retroviral vector which encode green fluorescent protein (eGFP). Stable cell line was selected with antibiotic, G418. About 99.6% G418 resistant cells were eGFP positive after section.

The subject's peripheral blood mononuclear cells (PBMCs) were prepared by clinical study sites and received in BD Vacutainer Cell Preparation Tube with sodium heparin (Product Number: 362753, Becton Dickinson, Franklin Lakes, N.J.).

Two-fold serial dilution of 800 µl effector cells (patient's PBMC) starting at concentration of $1\times10^6$ cells/mL were put into four individual polystyrene 12×75-mm tubes. Log phase growing target cells (K562/eGFP) were adjusted with growth medium (RPMI-1640) to a concentration of $1\times10^5$ cells/mL and 100 µL targets then added into the tubes to provide effector/target (E/T) ratios of 80:1, 40:1, 20:1, 10:1. Effector cells alone and target cells alone were used as controls. All tubes were incubated at 37° C. with 5% $CO_2$ for about 3.5 hr. Ten microliters of propidium iodide (PI) at a concentration of 1 mg/mL was added to each tube including effector and target control tubes and then incubated at room temperature for 15 min.

Cytotoxic activity was analyzed with a FACSCalibur flow cytometer (Becton Dickinson). Linear amplification of the forward and side scatter (FSC/SSC) signals, as well as logarithmic amplification of eGFP and PI emission in green and red fluorescence were obtained. Ten thousand events per sample tube with no gating for acquisition were collected for analysis. Data analysis for two-parameter dot plots for eGFP versus PI was performed using CELLQuest (Becton Dickinson Biosciences) software to enumerate live and dead target cells. Debris and dead cells were excluded by setting a threshold of forward light scatter.

Example 3

The Disclosed Combination Therapy Induces Hsp70

A Phase I trial was conducted for combined administration of a bis(thio-hydrazide) amide (Compound (1)) and a taxane (paclitaxel) to human subjects with various advanced solid tumors. Compound (1) and paclitaxel were co-administered intravenously over 3 hours every 3 weeks. Starting doses were 44 milligrams/meter$^2$ (mg/m2, or 110 micromoles/meter$^2$ (µmol/m2)) Compound (1) and 135 mg/m2 (158 µmol/m2) paclitaxel. Paclitaxel was then increased to 175 mg/m2 (205 µmol/m2), followed by escalation of Compound (1) to establish the maximum tolerated dose based on first cycle toxicity in 3 to 6 patients at each dose level. Pharmacokinetic (PK) studies were performed during cycle 1 using liquid chromatography/mass spectrometry (LC/MS) to measure both compounds in plasma. Heat shock protein 70 (Hsp70) was measured in plasma before and after treatment. 35 patients were evaluated at 8 dose levels, including paclitaxel at 135 mg/m2 (158 mmol/m2) and Compound (1) at 44 mg/m2, and paclitaxel at 175 mg/m2 (205 µmol/m2) and Compound (1) at a doses ranging among 44-525 mg/m2 (110-1311 µmol/m2). Table 1 shows the eight different doses #1-#8 in mg/m$^2$ and µmol/m$^2$.

TABLE 1

|  | #1 | #2 | #3 | #4 | #5 | #6 | #7 | #8 |
|---|---|---|---|---|---|---|---|---|
| Compound (1), mg/m$^2$ | 44 | 44 | 88 | 175 | 263 | 350 | 438 | 525 |
| Compound (1), µmol/m$^2$ | 110 | 110 | 220 | 437 | 657 | 874 | 1094 | 1311 |
| Paclitaxel, mg/m$^2$ | 135 | 175 | 175 | 175 | 175 | 175 | 175 | 175 |
| Paclitaxel, µmol/m$^2$ | 158 | 205 | 205 | 205 | 205 | 205 | 205 | 205 |

No serious effects specifically attributable to Compound (1) were observed. Paclitaxel dose limiting toxicities occurred in a single patient in each of the top three dose levels (neutropenia, arthralgia, and febrile neutropenia with mucositis) resulting in cohort expansion. Compound (1) exhibited linear PK that was unaffected by paclitaxel dose, and was rapidly eliminated from plasma with terminal-phase half life of 0.94±0.23 hours (h) and total body clearance of 28±8 Liters/hour/meter$^2$ (L/h/m$^2$). Its apparent volume of distribution was comparable to total body water ($V_{ss}$ 23±16 L/m$^2$). Paclitaxel PK appeared to be moderately dependent on the Compound (1) dose, as indicated by a significant trend toward decreasing clearance, and increase in peak plasma concentration and VS, but without affecting the terminal phase half-life. These observations are consistent with competitive inhibition of paclitaxel hepatic metabolism. Increased toxicity at higher dose levels was consistent with a moderate increase in systemic exposure to paclitaxel. Induction of Hsp70 protein in plasma was dose dependent, peaking between about 8 hours to about 24 hours after dosing.

Figure 1B:
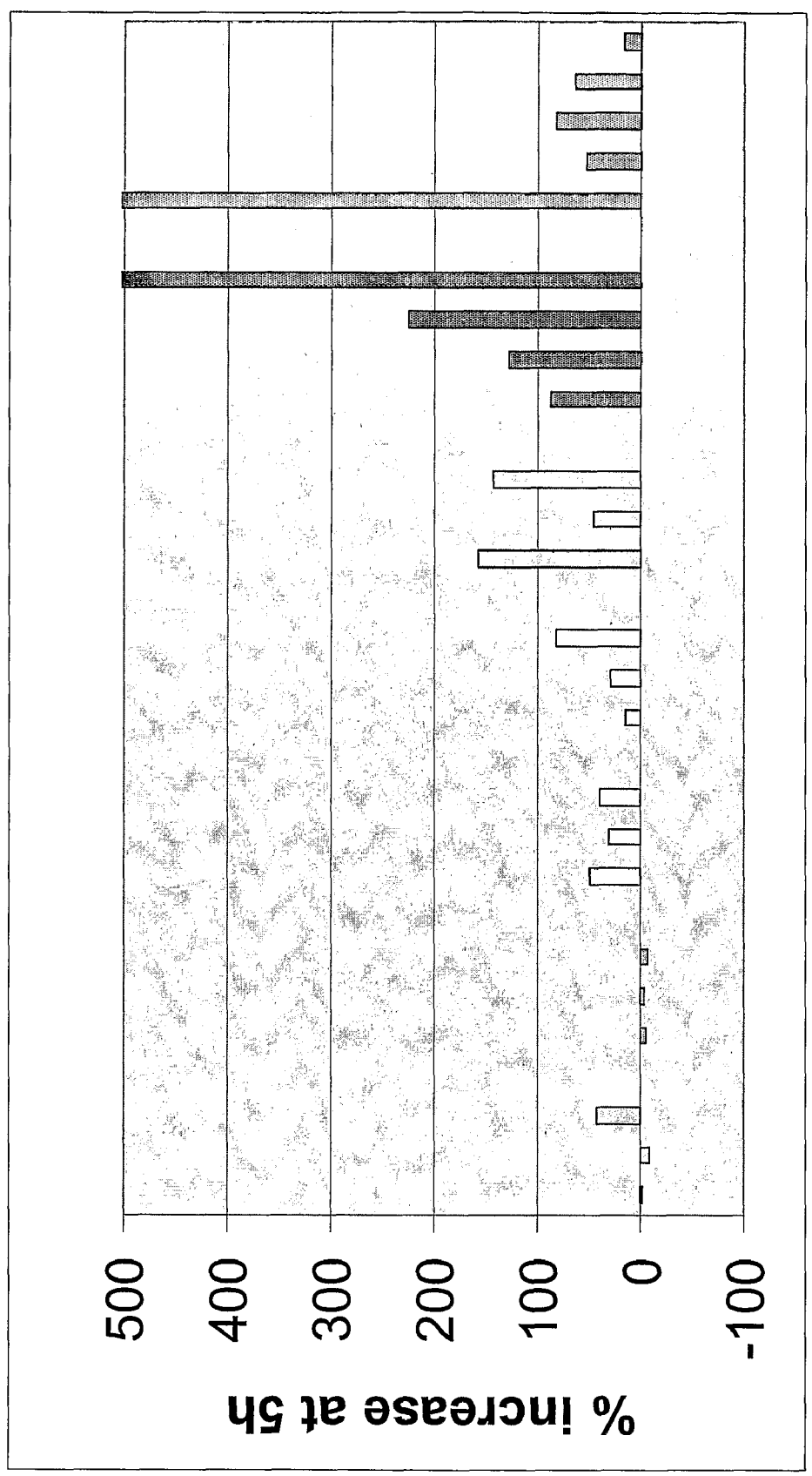
Figure 1C:
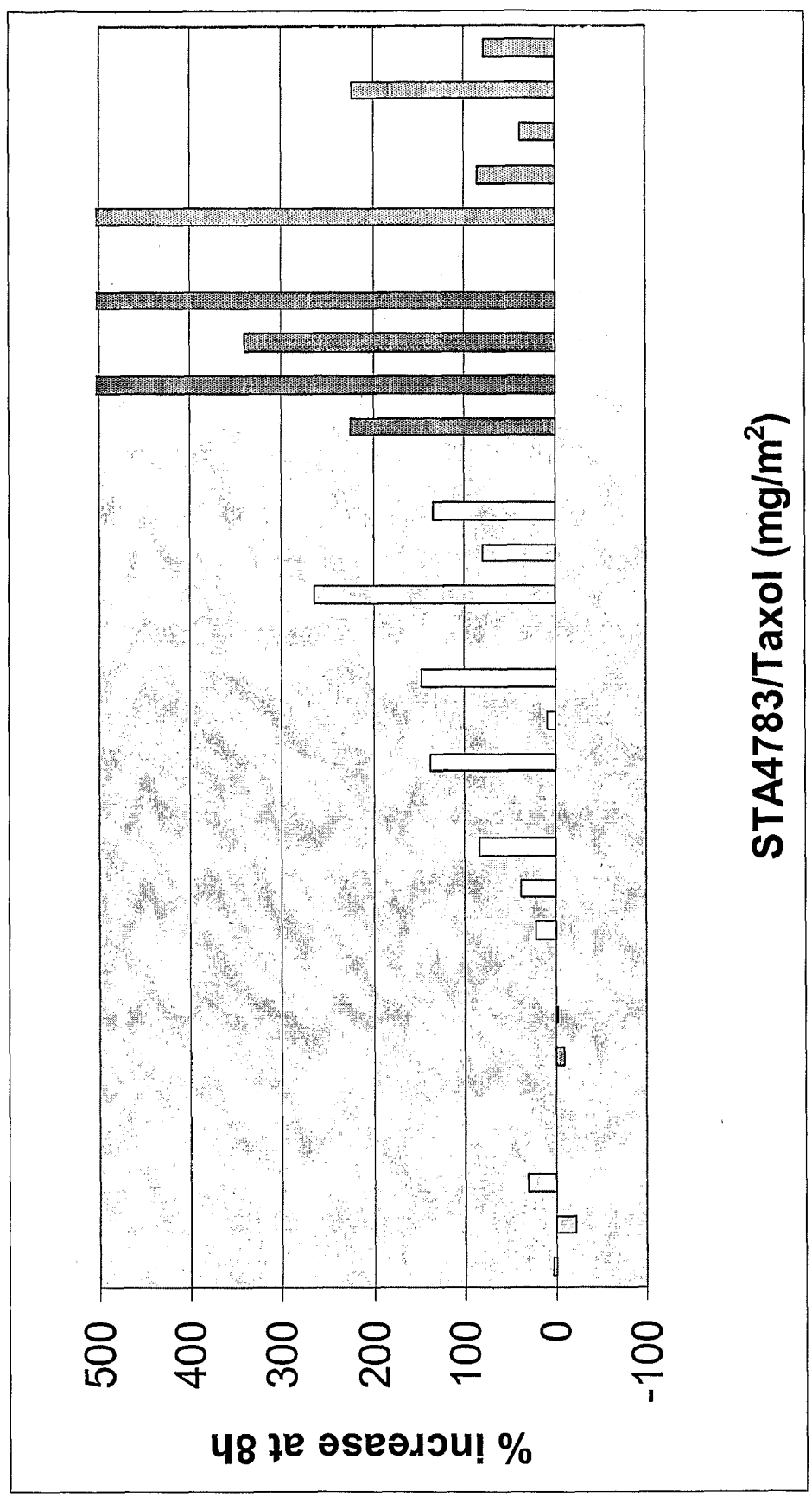

FIGS. 1A, 1B, and 1C are bar graphs showing the percent increase in Hsp70 plasma levels associated with administration of the Compound (1)/paclitaxel combination therapy at 1 hour (FIG. 1A), 5 hours (FIG. 1B), and 8 hours (FIG. 1C) after administration. Significant rises in Hsp70 levels occurred for at least one patient at the 88 mg/m2 (220 µmol/m2) Compound (1) dose, where Hsp70 levels nearly doubled in a percent increase of about 90%. At the 175 mg/m2 (437 µmol/m2) Compound (1) dose, Hsp70 concentrations more than doubled in two patients; at the 263 mg/m2 (657 µmol/m2) Compound (1) dose, Hsp70 concentrations roughly doubled in two patients and increased by more than 250% in a third patient; at the 350 mg/m2 (874 µmol/m2) Compound (1) dose, Hsp70 concentrations increased more than 200% in all patients and increased by as much as 500% in two patients; at the 438 mg/m2 (1094 µmol/m2) Compound (1) dose, Hsp70 concentrations roughly doubled in two patients, increased by over 200% in one patient, and increased by as much as 500% in another patient.

Time to progression will be measured as the time from patient randomization to the time the patient is first recorded as having tumor progression according to the RECIST (Response Evaluation Criteria in Solid Tumors Group) criteria; see Therasse P, Arbuck S G, Eisenhauer E A, Wanders J, Kaplan R S, Rubinstein L, et al. New guidelines to evaluate the response to treatment in solid tumors. J Natl Cancer Inst 2000; 92:205-16, the entire teachings of which are incorporated by reference. Death from any cause will be considered as progressed.

Time to progression can be performed on the randomized sample as well as the efficacy sample. Treatment groups can be compared using the log-rank test and Kaplan-Meier curves of time to progression can be presented.

Thus, the combination of a bi(thio-hydrazide) amide and taxane dramatically increased plasma Hsp70 levels in patients, giving significant increases for patients at a combined paclitaxel dose of 175 mg/m2 (205 µmol/m2) and Compound (1) doses ranging from 88 through 438 mg/m2 (220-1094 µmol/m2). Moreover, the combination was well-tolerated, with adverse events consistent with those expected for paclitaxel alone.

Example 4

A 2 Stage Phase 2 Study Shows the Disclosed Combination Therapy is Effective for Treating Advanced Metastatic Melanoma The following study of Compound (1) and paclitaxel in patients with advanced metastatic melanoma was initiated based on the biological activity shown by the results of the above Phase I study, where the combined administration Compound (1) and paclitaxel led to dose-related Hsp70 induction.

The study included a Stage 1 initial safety assessment of the weekly dose schedule, where Compound (1) 106 mg/m2 (265 µmol/m2) and paclitaxel at 80 mg/m2 (94 µmol/m2) were administered weekly for 3 weeks out a 4 week period. The dose of Compound (1) was then escalated to 213 mg/m2 (532 µmol/m2) in combination with the paclitaxel at 80 mg/m2 (94 µmol/m2). The higher tolerated dose level was expanded to a total of 20 patients (Stage 1).

A total of 7 patients were treated in the initial safety assessment, 3 at the lower dose level and 4 at the higher. In the absence of dose-limiting toxicities in either group, the higher dose level was chosen as the dose of interest and additional patients were enrolled to complete stage 1. Adverse events seen were as expected for paclitaxel chemotherapy administration. Of 20 evaluable patients, 11 were stable at 3 months for 55% NPR.

The study will continue to Stage 2 if 7 or more patients have a response of stable disease or better, or at least 2 patients have a partial response or better. A safety assessment was performed with the first 6 patients enrolled a s the weekly dose schedule had not previously been studied in humans. The primary endpoint is non-progression rate (NPR) at 3 months and response rate. Pharmacodynamic parameters include pre and post-dose NK cell activity in blood and when possible, tumor biopsies.

Table 2 shows the significant preliminary results of anti-cancer efficacy and NK cell activity results when assayed 7 days after the second dose for different subjects. The Effector/Target data shows the ratio of the subjects PBMC cells to the NK assay target cells. The pre and post dose column values show the percent of tumor cells lysed before dosing with Paclitaxel and Compound (1). Best Response indicates an evaluation of the patient's tumor: SD indicates less than 20% of an increase and less than 30% of a decrease in the sum of the longest diameters as compared to baseline; and PD=at least a 20% increase in the sum of the longest diameters as compared to baseline. NK Activity indicates the change in NK activity before and after dosing.

Table 2 shows that for patients completing the study (#12-#20, #22), three patients had less than 20% of an increase and less than 30% of a decrease in the sum of the longest diameters as compared to baseline, while seven patients had at least a 20% increase in the sum of the longest diameters as compared to baseline. For NK cell activity, four of the original patients showed a statistically significant increase between pre- and post-dose treatment.

TABLE 2

| Subject | Effector/ Target | % tumor cell lysis pre-dose | % tumor cell lysis post-dose | dosing information Paclitaxel, mg/M² | Cmpnd (1) mg/M² | Best Response cycle 2 | NK activity |
|---|---|---|---|---|---|---|---|
| 12 | 80:1 | 2.32 | 7.74 | 80 | 106 | SD | increase |
| 13 | 80:1 | 6.13 | 2.43 | 80 | 106 | PD | decrease |
| 14 | 80:1 | 3.83 | 10.77 | 80 | 213 | SD | increase |
| 15 | (40:1) | 3.5 | 10.01 | 80 | 213 | PD | (increase) |
| 16 | 80:1 | 19.71 | 19.78 | 80 | 213 | SD | no change |
| 17 | 80:1 | 41.61 | 26.52 | 80 | 213 | PD | decrease |
| 18 | 80:1 | 8.6 | 8.64 | 80 | 213 | PD | no change |
| 19 | 80:1 | 24.76 | 18.77 | 80 | 213 | PD | decrease |
| 20 | 80:1 | 16.49 | 5.2 | 80 | 213 | PD | decrease |
| 21 | 80:1 | 15.4 | 26.31 | 80 | 213 | NA | increase |
| 22 | 80:1 | 10.81 | 7.2 | 80 | 213 | PD | decrease |

The combination therapy was well-tolerated on the weekly schedule. Enrollment in the randomized portion will assess the activity of Compound (1) in combination with paclitaxel versus paclitaxel alone.

Stage 2 is planned to be a randomized 2-arm study comparing the drug combination to paclitaxel alone. The criterion for continuation to Stage 2 is >=50% non-progression rate (NPR) at two months. A total of 78 patients are to be randomized 2:1 (combination:control). The primary endpoint is time to progression; secondary endpoints are response rate, survival, and quality of life. Pharmacodynamic parameters will include pre- and post-dose measurements of NK cell activity in blood and, when possible, tumor biopsies.

Example 5

A Phase 2 Study Shows the Disclosed Combination Therapy is Effective for Treating Soft Tissue Sarcomas The following study of Compound (1) and paclitaxel in patients with soft tissue sarcomas was initiated based on the biological activity shown by the results of the above Phase I study, where the combined administration Compound (1) and paclitaxel led to dose-related Hsp70 induction.

The study is a 2 stage design, enrolling 30 patients in the first stage and adding 50 patients to total 80 if certain continuation criteria are met. Major inclusion criteria are refractory or recurrent soft tissue sarcomas other than gastrointestinal stromal tumor (GIST), with evidence of recent progression. Patients are treated weekly, 3 weeks out of every 4 week cycle with 213 mg/m2 Compound (1) and 80 mg/m2 paclitaxel. For example, the compounds were administered together 3 weeks out of 4 on Days 1, 8, and 15 of a 28 day cycle as a 1 hour IV infusion. 30 Patients have been enrolled to completed accrual of Stage 1.

As used herein, "soft-tissue sarcomas" (STS) are cancers that begin in the soft tissues that support, connect, and surround various parts of the body for example, soft tissues such as muscles, fat, tendons, nerves, and blood vessels, lymph nodes, or the like. Such STSs can occur anywhere in the body, though typically about one half occur in the limbs. In various embodiments, STSs can include one or more cancers selected from liposarcoma, fibrosarcoma, malignant fibrous histiocytoma leiomyosarcoma, neurofibrosarcoma, rhabdomyosarcoma, synovial sarcoma, or the like.

Table 3 shows the significant preliminary results of anticancer efficacy and NK cell activity results when assayed 7 days after the second dose for different subjects. The Effector/Target data shows the ratio of the subjects PBMC cells to the NK assay target cells. The pre and post dose column values show the percent of tumor cells lysed before dosing with Paclitaxel and Compound (1). Best Response indicates an evaluation of the patient's tumor: PR=at least a 30% decrease in the sum of the longest diameters as compared to baseline; SD indicates less than 20% of an increase and less than 30% of a decrease in the sum of the longest diameters as compared to baseline; and PD=at least a 20% increase in the sum of the longest diameters as compared to baseline. NK Activity indicates the change in NK activity before and after dosing.

Table 3 shows that for patients completing the study (#23-#29, #31-33), five patients had less than 20% of an increase and less than 30% of a decrease in the sum of the longest diameters as compared to baseline, while five patients had at least a 20% increase in the sum of the longest diameters as compared to baseline. For NK cell activity, seven of the original patients showed a statistically significant increase or no change between pre- and post-dose treatment, while only four of the original patients showed a decrease statistically significant increase between pre- and post-dose treatment.

TABLE 3

| Subject | Effector/ Target | % tumor cell lysis pre-dose | % tumor cell lysis post-dose | dosing information Paclitaxel, mg/M² | Cmpnd (1) mg/M² | Best Response cycle 2 | NK activity |
|---|---|---|---|---|---|---|---|
| 23 | 80:1 | 4.28 | 30.48 | 80 | 213 | PD | increase |
| 24 | 80:1 | 20.74 | 20.04 | 80 | 213 | SD | no change |
| 25 | 80:1 | 34.28 | 11.86 | 80 | 213 | PD | decrease |
| 26 | 80:1 | 22.33 | 14.74 | 80 | 213 | SD | decrease |
| 27 | 80:1 | 10.6 | 22.9 | 80 | 213 | SD | increase |
| 28 | 80:1 | 17.93 | 28.13 | 80 | 213 | SD | increase |
| 29 | 80:1 | 6.58 | 17.18 | 80 | 213 | PD | increase |
| 30 | (40:1) | 9.88 | 9.91 | 80 | 213 | NA | no change |
| 31 | 80:1 | 2.62 | 5.46 | 80 | 213 | SD | increase |
| 32 | 80:1 | 13.03 | 7.41 | 80 | 213 | PD | decrease |
| 33 | 80:1 | 15.77 | 7.84 | 80 | 213 | PD | decrease |

Patients are currently being evaluated through 3 months. Adverse events seen were typical for paclitaxel administration on a similar schedule. Assessment of NK activity is ongoing. The addition of Compound (1) to the weekly paclitaxel schedule was well-tolerated. Stage 1 accrual has completed, and patients are currently being evaluated for the study continuation decision.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating a human with metastatic melanoma, comprising the step of co-administering to the human over three to five weeks:
   paclitaxel in an amount of between about 243 µmol/m² to 315 µmol/m²; and
   a bis(thiohydrazide amide) in an amount between about 1473 µmol/m² and about 1722 µmol/m², wherein the bis(thiohydrazide amide) is represented by the following Structural Formula:

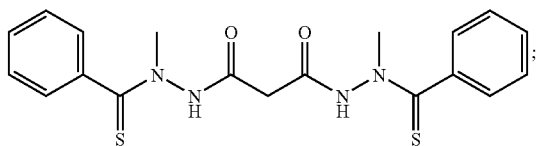

or a pharmaceutically acceptable salt thereof.

2. The method of claim 1, wherein the paclitaxel and the bis(thio-hydrazide) amide are each administered in three equal weekly doses for three weeks of a four week period.

3. The method of claim 2, further comprising repeating the four week administration period until the cancer is in remission.

4. The method of claim 3, wherein the paclitaxel is intravenously administered in a weekly dose of about 94 μmol/m$^2$.

5. The method of claim 2, wherein the bis(thiohydrazide amide) is intravenously administered in a weekly dose of between about 500 μmol/m$^2$ and about 562 μmol/m$^2$.

6. The method of claim 3, wherein the bis(thiohydrazide amide) is intravenously administered in a weekly dose of about 532 μmol/m$^2$.

7. The method of claim 1, wherein the bis(thiohydrazide amide) is:
the disodium or dipotassium salt.

8. A method of treating a human with cancer, comprising intravenously administering to the human in a four week period, three equal weekly doses of the paclitaxel in an amount of about 94 μmol/m$^2$ and a bis(thiohydrazide amide) represented by the following Structural Formula:

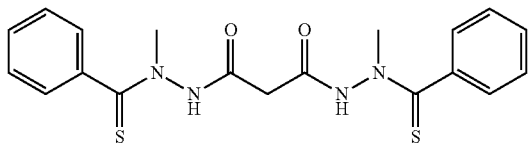

or a pharmaceutically acceptable salt thereof in an amount of about 532 μmol/m$^2$,
wherein the cancer is metastatic melanoma.

* * * * *